United States Patent
Romines, III et al.

(10) Patent No.: US 6,525,050 B1
(45) Date of Patent: Feb. 25, 2003

(54) (4-OXO-2-PYRIMIDINYL)THIOALKYL COMPOUNDS USEFUL AS AICARFT INHIBITORS

(75) Inventors: William H. Romines, III, San Diego, CA (US); Michael D. Varney, Solana Beach, CA (US); Cynthia L. Palmer, La Mesa, CA (US); Ted M. Bleckman, La Jolla, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/786,109

(22) PCT Filed: Sep. 3, 1999

(86) PCT No.: PCT/US99/20331
§ 371 (c)(1), (2), (4) Date: Mar. 1, 2001

(87) PCT Pub. No.: WO00/13688
PCT Pub. Date: Mar. 16, 2000

Related U.S. Application Data

(60) Provisional application No. 60/099,259, filed on Sep. 4, 1998.

(51) Int. Cl.[7] .................... C07D 239/02; C07D 413/02; C07D 413/04
(52) U.S. Cl. .................... 514/235.8; 514/274; 544/123; 544/310; 544/311; 544/312; 544/314
(58) Field of Search .................... 514/274, 235.8; 544/310, 311, 312, 123, 314

(56) References Cited

FOREIGN PATENT DOCUMENTS

| | | | |
|---|---|---|---|
| EP | 0391254 | | 10/1990 |
| JP | 6-206806 | * | 7/1994 |
| WO | WO 94/13295 | | 6/1994 |

OTHER PUBLICATIONS

Faessel HM, Slocum HK, Jackson RC, Boritzki TJ, Rustum YM, Nair MG, Greco WR. "Super in vitro synergy between inhibitors of dihydrofolate reductase and inhibitors of other folate–requiring enzymes: the critical role of polyglutamylation", Cancer Res. 1998.*

Draetta, G. and Pagano, M. in "Annual Reports in Medicinal Chemistry, vol. 31", 1996, Academic Press, San Diego, p. 241–246.*

Khalil, Zarif Hallem; Abdel Hafez, Ali Ahmed; Abdo Ahmed, Ahmed, Phosphorus, Sulfur Silicon Relat. Elem., 45(1–2), 81–93 (English) 1989.*

* cited by examiner

Primary Examiner—Mukund J. Shah
Assistant Examiner—Thomas C McKenzie
(74) Attorney, Agent, or Firm—Karl Neidart; Bryan C. Zielinski; Peter Richardson

(57) ABSTRACT

Compounds of the formula:

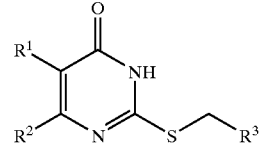

(where $R^1$, $R^2$ and $R^3$ are defined in the specification) are inhibitors of AICARFT. These compounds, as well as their pharmaceutically acceptable salts, solvents, prodrugs, and pharmaceutically active metabolites, are useful in pharmaceutical compositions for treating diseases such as cancer.

4 Claims, No Drawings

(4-OXO-2-PYRIMIDINYL)THIOALKYL COMPOUNDS USEFUL AS AICARFT INHIBITORS

This application is a national phase filing under 35 U.S.C. § 371 of International Patent Application No. PCT/US99/20331, filed Sep. 3, 1999, and a continuation-in-part of U.S. Provisional Patent Application No. 60/099,259, filed Sep. 4, 1998, the disclosures of each of which are incorporated herein by reference.

FIELD AND INDUSTRIAL APPLICABILITY OF THE INVENTION

The present invention relates to compounds that inhibit the enzyme aminoimidazole carboxamide ribonucleotide formyl transferase (AICARFT), to pharmaceutical compositions containing these compounds, and to their use to inhibit AICARFT. The-invention also relates to the preparation of these compounds, and to intermediates for preparing these compounds.

BACKGROUND OF THE INVENTION

The large class of antiproliferative agents includes antimetabolite compounds. A particular subclass of antimetabolites known as antifolates or antifoles are antagonists of the vitamin folic acid.

Aminoimidazole carboxamide ribonucleotide formyl transferase (AICARFT) is a folate-dependent enzyme in the de novo purine biosynthesis pathway. This pathway is critical to cell division and proliferation. Shutting down this pathway is known to have an antiproliferative, in particular, an antitumor effect.

There is a need for compounds that inhibit the enzyme AICARFT, having antitumor, antiinflammatory, antipsoriatic, and/or immunosuppressive activity.

SUMMARY OF THE INVENTION

An object of the invention is to provide small-molecule compounds that inhibit AICARFT. Another object of the invention is to provide antitumor, antiinflammatory, antipsoriatic, or immunosuppressive agents useful in pharmaceutical treatments.

Surprisingly, such objects have been achieved by the compounds of formula I:

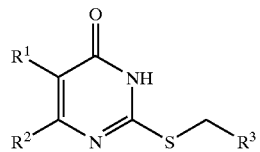

(I)

wherein:
  $R^1$ is H or CN;
  $R^2$ is phenyl or thienyl, each of which may be optionally substituted with phenyl, phenoxy, thienyl, tetrazolyl, or 4-morpholinyl; and
  $R^3$ is phenyl substituted with —$SO_2NR^5R^6$ or —$NR^5SO_2R^6$ and optionally further substituted by one or more of the suitable substituents defined below; wherein $R^5$ is H or lower alkyl, $R^6$ is lower alkyl, substituted or unsubstituted heteroarylalkyl, substituted or unsubstituted aryl, or substituted or unsubstituted heteroaryl, wherein the aryl and heteroaryl moieties may be substituted by one or more of the suitable substituents defined below; or

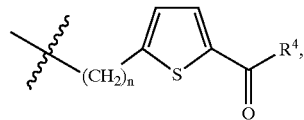

wherein n is an integer of from 1 to 4, $R^4$ is OH, lower alkoxy, or a glutamic-acid or glutamate-ester moiety linked through the amine functional group.

The invention also relates to pharmaceutically acceptable salts, solvates, prodrugs, and active metabolites of compounds of the formula I.

In preferred embodiments, $R^2$ is selected from

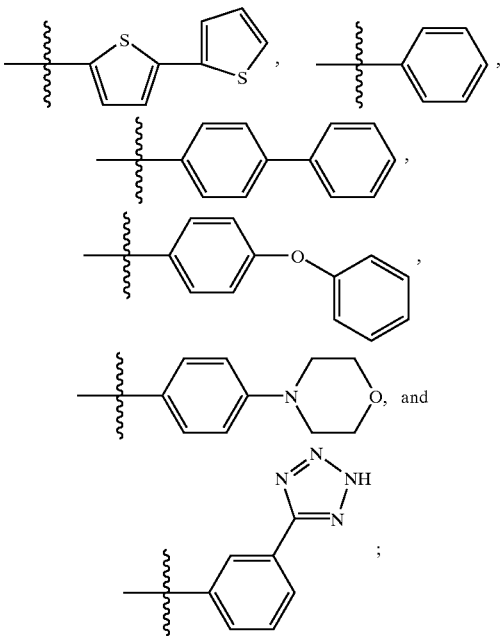

and/or $R^3$ may be phenyl substituted with —$SO_2NR^5R^6$ or —$NR^5SO_2R^6$ and optionally further substituted by lower alkyl, lower alkoxy, or halogen. For example, $R^3$ may be:

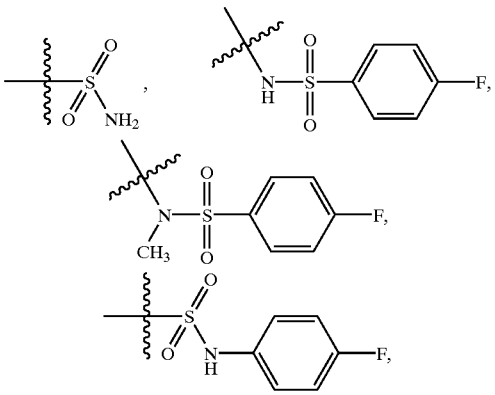

3
-continued
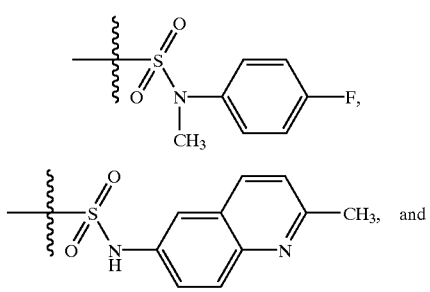
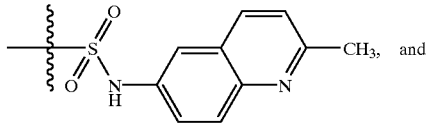
4
-continued
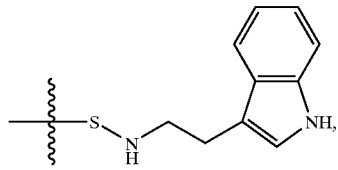
each of which may be optionally substituted with one additional substituent selected from methyl, methoxy and chloro.
Perferred compounds of the invention are:
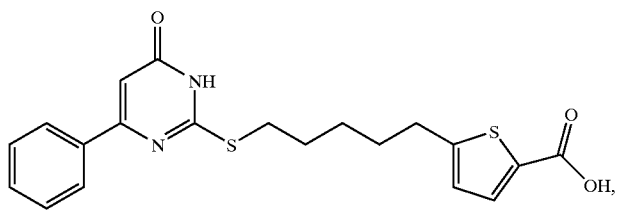
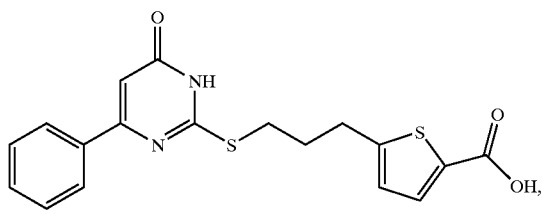
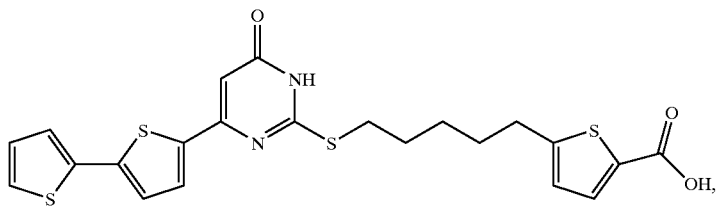
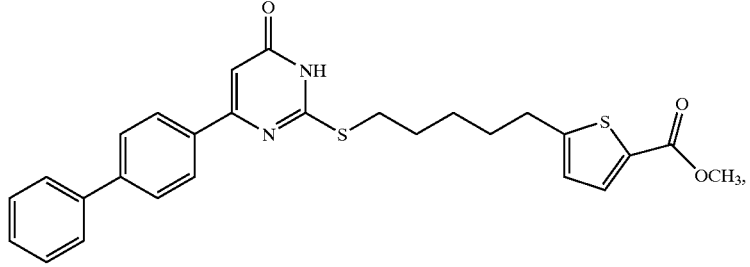
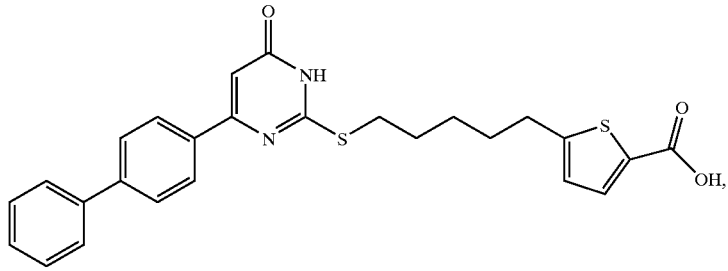

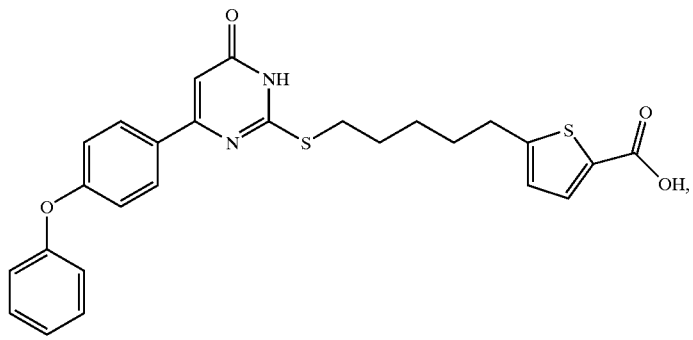
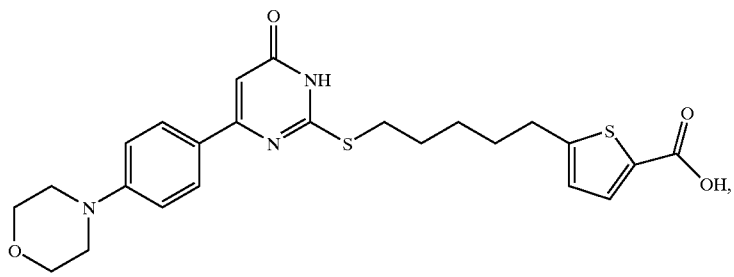
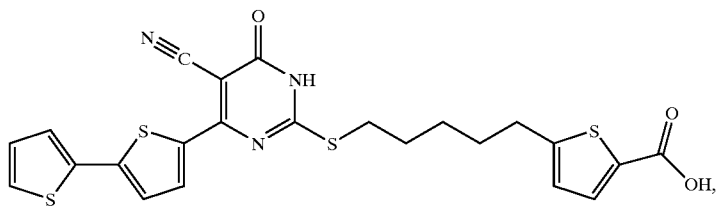
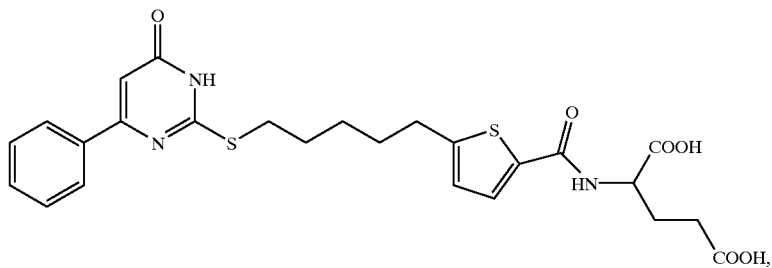
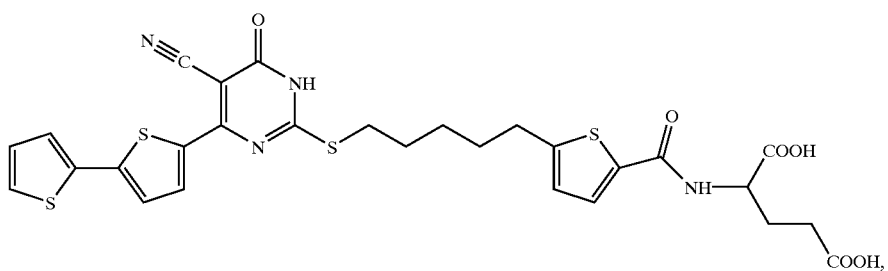
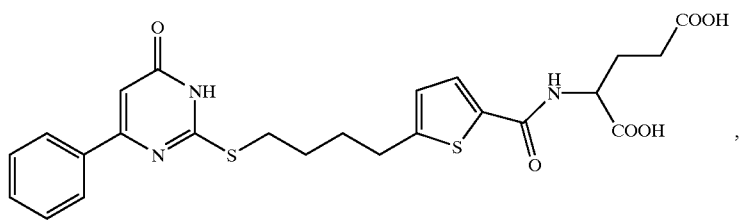

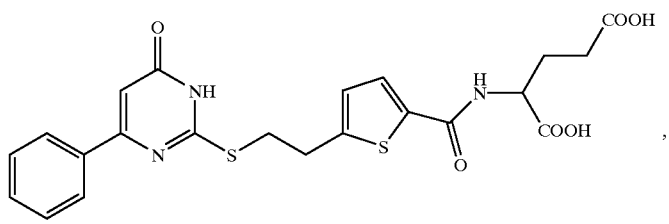
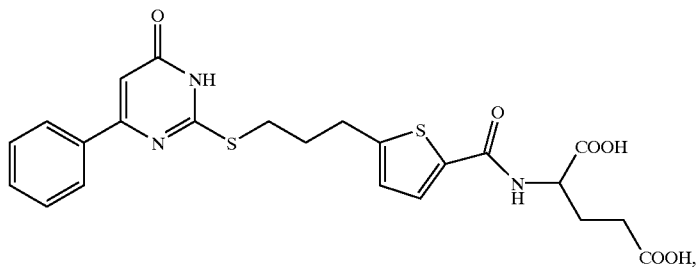
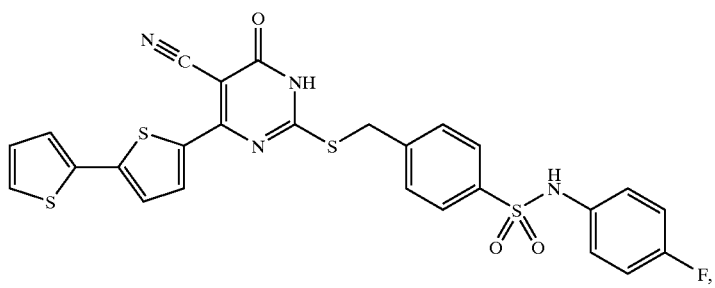
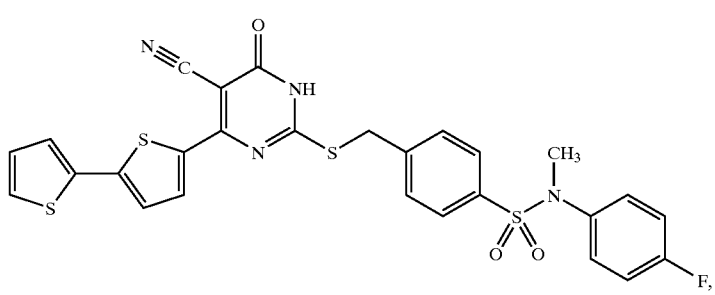
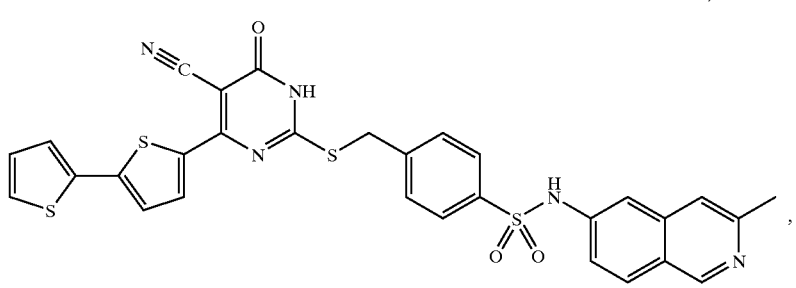
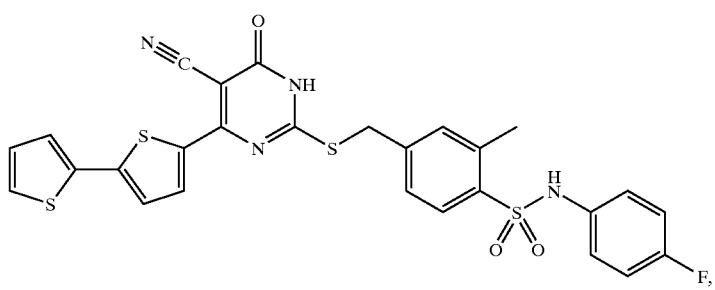

-continued
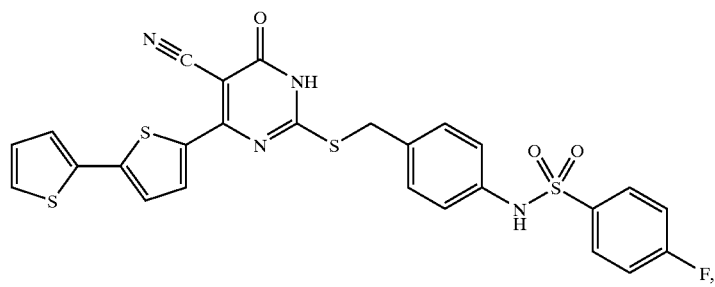
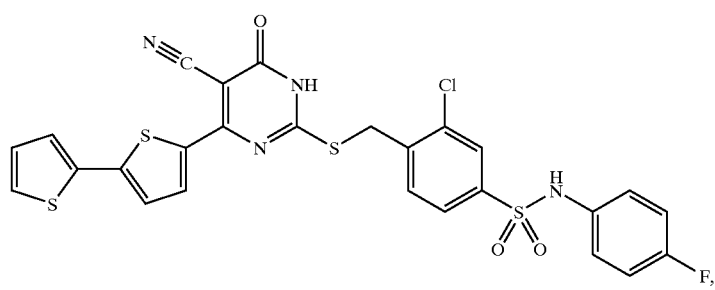
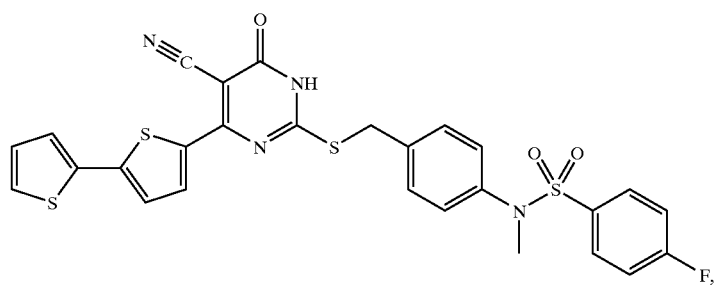
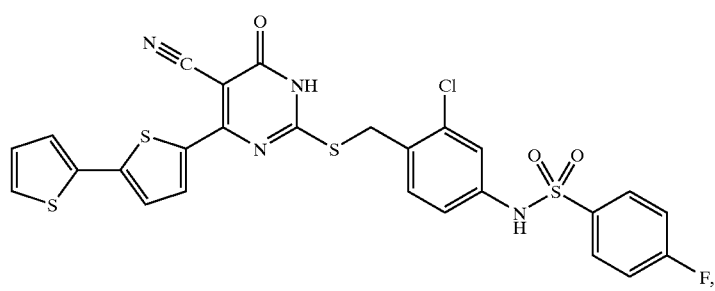
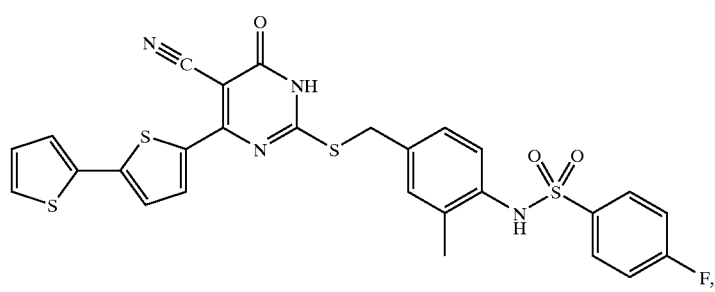
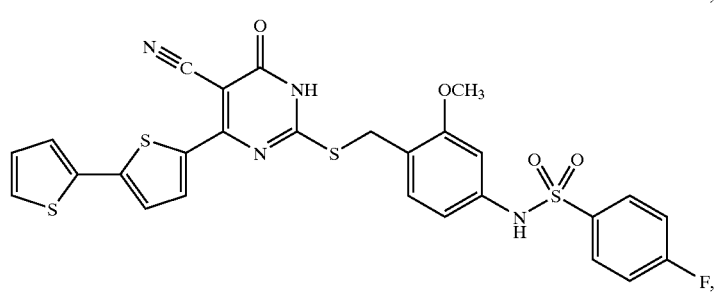

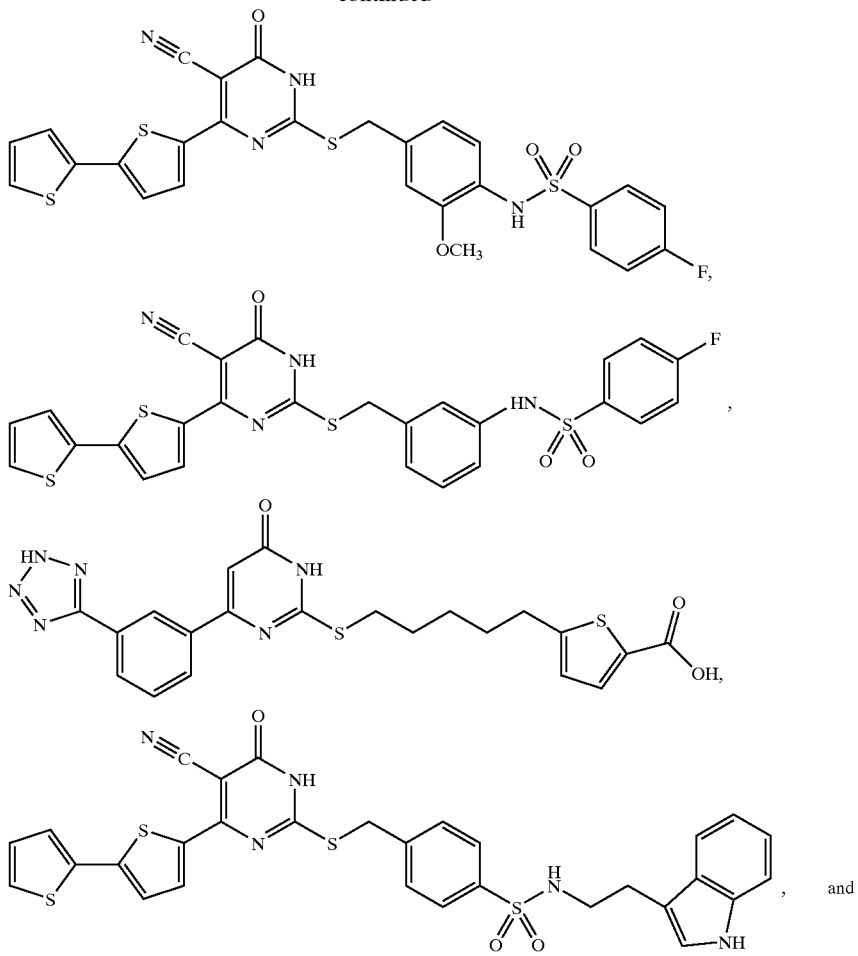

and pharmaceutically acceptable salts, solvates, prodrugs, and active metabolites of such compounds.

The invention further relates to use of the compounds of formula I, and especially the above-described preferred compounds, as inhibitors of the enzyme AICARFT.

The invention also relates to methods of synthesizing the compounds of the invention, comprising carrying out the following general alkylation reaction:

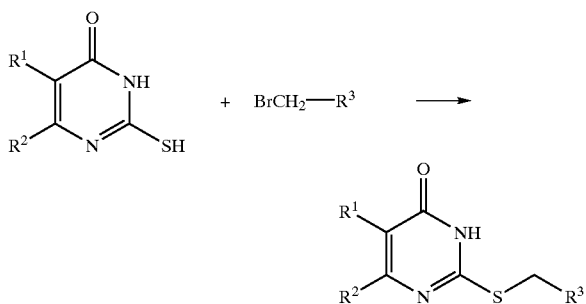

where $R^1$, $R^2$, and $R^3$ are as defined above.

Other features, objects, and advantages of the invention will become apparent from the detailed description of the invention provided below.

DETAILED DESCRIPTION AND PREFERRED EMBODIMENTS

In accordance with a convention used in the art, ⌇ is used in structural formulae herein to depict the bond that is the point of attachment of the moiety or substituent to the core or backbone structure.

Where chiral carbons are included in chemical structures, unless a particular orientation is depicted, both stereoisomeric forms are intended to be encompassed. Further, the inventive compounds may exist as single stereoisomers, racemates, and/or mixtures of enantiomers and/or diastereomers. All such single stereoisomers, racemates, and mixtures thereof are intended to be within the broad scope of the present invention. Preferably, however, the inventive compounds are used in optically pure form.

As generally understood by those skilled in the art, an optically pure compound is one that is essentially enantiomerically pure. Preferably, an optically pure compound of the invention contains at least 90% of a single isomer (80% enantiomeric excess), more preferably at least 95% (90% e.e.), even more preferably at least 97.5% (95% e.e.), and most preferably at least 99% (98% e.e.).

The compounds illustrated by the chemical formulae referred to herein may exhibit the phenomenon of tautomerism. Although the structural formulae depict one of the possible tautomeric forms, it should be understood that the invention nonetheless encompasses all tautomeric forms.

As used herein, the term "alkyl group" is intended to mean a straight- or branched-chain monovalent radical of saturated and/or unsaturated carbon atoms and hydrogen atoms, such as methyl (Me), ethyl (Et), propyl, isopropyl, butyl, isobutyl, t-butyl, ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable substituents as defined below (e.g., one or more halogens, such as F, Cl, Br, or I, with F and Cl being preferred). A "lower alkyl group" is intended to mean an alkyl group having from 1 to 4 carbon atoms in its chain.

An "alkoxy group" is intended to mean the radical —$OR_a$, where $R_a$ is an alkyl group. Exemplary alkoxy groups include methoxy, ethoxy, and propoxy. "Lower alkoxy" refers to alkoxy groups wherein the alkyl portion has 1 to 4 carbon atoms.

An "aryl" group is intended to mean a cyclic aromatic hydrocarbon group, such as phenyl or naphthyl, which may be unsubstituted or substituted by one or more of the suitable substituents defined below (e.g., with one or more halogen, lower alkyl, and/or lower alkoxy group). Preferably, aryl is a substituted or unsubstituted phenyl group.

A "heteroaryl" group is intended to mean a cyclic aromatic group containing at least one heteroatom selected from oxygen, sulfur and nitrogen, wherein any position of the heteroaryl group may be unsubstituted or substituted by a suitable substituent, as defined below (e.g., with a halogen, lower alkyl, or lower alkoxy group). Preferably the heteroaryl group is a nitrogen-containing cyclic aromatic group. Exemplary nitrogen-containing heteroaryl groups include quinolyl, isoquinolyl, indolyl, pyridyl, pyrrolyl, pyrazinyl, and thiazolyl. A "heteroarylalkyl" group comprises an alkylenyl moiety bonded to a substituted or unsubstituted heteroaryl group, e.g., —$(CH_2)_x$-indolyl, wherein x may be an integer of from 1 to 4 and any position of the heteroaryl group may be unsubstituted or substituted by a suitable substituent, as defined below. Preferable heteroaryl groups include substituted or unsubstituted isoquinolyl or indolyl groups.

The term "substituent" or "suitable substituent" is intended to mean any suitable substituent that may be recognized or selected, such as through routine testing, by those skilled in the art. Illustrative examples of suitable substituents include hydroxy groups, halogens, oxo groups, alkyl groups, acyl groups, sulfonyl groups, mercapto groups, alkylthio groups, alkoxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted with one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

A "prodrug" is intended to mean a compound that is converted under physiological conditions or by solvolysis or metabolically to a specified compound that is pharmaceutically active.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine.

A "pharmaceutically active metabolite" is intended to mean a pharmacologically active product produced through metabolism in the body of a specified compound.

A "pharmaceutically acceptable salt" is intended to mean a salt that retains the biological effectiveness of the free acids and bases of the specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formnates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, mandelates, and mesylates.

If a compound is a base, a desired salt may be prepared by any suitable method known in the art, including treatment of the free base with an inorganic acid, such as hydrochloric acid; hydrobromic acid; sulfuric acid; nitric acid; phosphoric acid; and the like; or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; or the like.

If a compound is an acid, a desired salt may be prepared by any suitable method known in the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different crystal forms, all of which are intended to be within the scope of the present invention and specified formulae.

The present invention is also directed to a method of inhibiting AICARFT activity, comprising contacting the enzyme with an effective amount of a compound of formula I, or a pharmaceutically acceptable salt, prodrug, pharmaceutically active metabolite, or solvate thereof. For example, AICARFT activity may be inhibited in mammalian tissue by administering a compound of formula I or a pharmaceutically acceptable salt, prodrug, pharmaceutically active metabolite, or solvate thereof. The compounds of formula I may also be used to inhibit the growth or proliferation of viruses and/or cells of higher organisms or microorganisms such as yeast, bacteria and fungi. The invention is also directed to methods of treating cancer by administering to a patient in need of such treatment an effective amount of a compound of the formula I, or a pharmaceutically acceptable salt, prodrug, pharmaceutically active metabolite, or solvate thereof.

"Treating" or "treatment" is intended to mean at least the mitigation of a disease condition in a mammal, such as a human, that is mediated by the inhibition of the activity of the target (e.g., reduction in tumor growth), and includes: (a) prophylactic treatment in a mammal, particularly when the mammal is found to be predisposed to having the disease condition but not yet diagnosed as having it; (b) inhibiting the disease condition; and/or (c) alleviating, in whole or in part, the disease condition.

The potency of the inventive compounds as inhibitors of AICARFT activity may be measured by any of the suitable methods known to those skilled in the art, including in vivo and in vitro assays. An example of a suitable assay for activity measurements is the AICARFT enzyme assay described herein.

Administration of the compounds of the formula I and their pharmaceutically acceptable prodrugs, salts, active metabolites, and solvates may be performed according to any of the accepted modes of administration available to those skilled in the art. Illustrative examples of suitable modes of administration include oral, nasal, parenteral, topical, transdermal, and rectal.

An inventive compound of formula I or a pharmaceutically acceptable salt, prodrug, active metabolite, or solvate thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use.

Acceptable methods of preparing suitable pharmaceutical forms of the pharmaceutical compositions are known or may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a non-aqueous or aqueous liquid suspension.

A dose of the pharmaceutical composition contains at least a therapeutically effective amount of the active compound or agent (i.e., a compound of formula I or a pharmaceutically acceptable salt, prodrug, active metabolite, or solvate thereof), and preferably is made up of one or more pharmaceutical dosage units. The selected dose may be administered to a mammal, for example, a human patient, in need of treatment mediated by inhibition of AICARFT activity, by any known or suitable method of administering the dose, including topically, for example, as an ointment or cream; orally; rectally, for example, as a suppository; parenterally by injection; or continuously by intravaginal, intranasal, intrabronchial, intraaural, or intraocular infusion.

An "effective amount" is intended to mean a therapeutic amount of an inventive compound that, when administered to a mammal in need of treatment, is sufficient to effect treatment for disease conditions alleviated by the inhibition of the target (i.e., AICARFT) activity, such as tumor growth. The amount of a given compound of the invention that will be therapeutically effective will vary depending upon factors such as the particular compound, the disease condition and the severity thereof, the identity of the mammal in need of treatment, which amount may be routinely determined by artisans.

An exemplary dose of a compound of the invention for a vertebrate host comprises an amount up to one gram of active compound per kilogram of the host, preferably one-half of a gram, more preferably 100 milligrams, and most preferably, about 50 milligrams or less, per kilogram of the host weight.

The pharmaceutical compositions of the invention may further comprise one or more other pharmaceutically active compounds. For example, for anticancer compositions, one of the following antitumor agents may be included: mitotic inhibitors (e.g., vinblastine); alkylating agents; dihydrofolate reductase inhibitors or thymidylate synthase inhibitors; antimetabolites (e.g., 5-fluorouracil, cytosinearabinoside); intercalating antibiotics (e.g. adriamycin, bleomycin); enyzmes (e.g., asparaginase); topoisomerase inhibitors (e.g., etoposide); and biological-response modifiers (e.g., interferon). The compositions of the invention may also comprise another enzyme inhibitor such as a GARFT inhibitor or antiproliferative agent, such as a compound described in U.S. Pat. No. 5,610,319 or U.S. Pat. No. 5,574,039, the disclosures of which are herein incorporated by reference. The compositions of the invention may also comprise one or more antibacterial, antifungal, antiparasitic, antiviral, antipsoriatic, or anticoccidial agent. Exemplary antibacterial agents include sulfonamides, such as sulfamethoxazole, sulfadiazine, sulfameter, or sulfadoxine; dihydrofolic reductase inhibitors, such as trimethoprim, bromodiaprim, or trimetrexate; penicillins; cephalosporins; and the quinolone carboxylic acids and their fused isothiazolo analogs.

The skeletal framework for the molecules of formula I may be assembled by the alkylation of the appropriate arylthiol with the corresponding alkyl bromide:

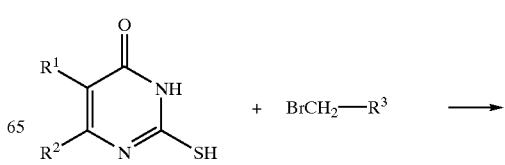

-continued

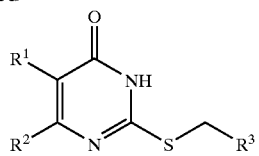

5-[(Arylthio)alkyl]thiophene-2-carboxylic acids and the 5-[(arylthio)alkyl]theno-2-yl glutamatic acids are prepared by the base-catalyzed hydrolysis of the requisite methyl esters and diethyl esters, respectively.

6-Phenyl-2-thiouracil is a commercially available aryl thiol; the other 6-aryl-4(3H)-oxopyrimidine-2-thiols are prepared by base-catalyzed condensation of the corresponding aroylacetate with thiourea. 5-Cyano-6-[5-(2-thienyl)thien-2-yl]-4(3H)-oxopyrimidine-2-thiol is synthesized from the condensation of equimolar amounts of 2,2'-bithiophene-5-carboxaldehyde, thiourea, ethyl cyanoacetate, and potassium carbonate.

The alkyl bromides are prepared from their alcohol precursors by treatment with carbon tetrabromide and triphenyl phosphine. In general, the 5-(hydroxyalkyl)thiophene-2-carboxylates and the [5-(hydroxyalkyl)theno-2-yl]glutamates are prepared by the palladium-catalyzed coupling of the requisite hydroxyalkyne with either methyl 5-bromothiophene-2-carboxylate or diethyl N-(5-bromotheno-2-yl)glutamate, followed by hydrogenation of the triple bond. The (hydroxymethyl)bisaryl sulfonamides are generally prepared by reduction of the corresponding methyl esters, which may be synthesized by sulfonylation of the appropriate aniline with the requisite sulfonyl chloride.

EXAMPLES

Specific examples of various preferred compounds of formula I and their preparation are described below. The structures of the compounds of the following examples were confirmed by one or more of the following: proton magnetic resonance spectroscopy, infrared spectroscopy, elemental microanalysis, mass spectrometry, thin layer chromatography, melting-point determination, and boiling-point determination. Where there is any discrepancy between the given structural formula shown for a compound and its chemical name provided, the structural formula is intended to apply.

Proton magnetic resonance ($^1$H NMR) spectra were determined using either a Bruker DPX 300 or a General Electric QE-300 spectrometer operating at a field strength of 300 megahertz (MHz). Chemical shifts are reported in parts per million (ppm, δ) downfield from an internal tetramethylsilane standard. Alternatively, $^1$H NMR spectra were referenced to residual protic solvent signals as follows: CHCl$_3$= 7.26 ppm; DMSO=2.49 ppm. Peak multiplicities are designated as follows: s=singlet; d=doublet; dd=doublet of doublets; ddd=doublet of doublet of doublets; t=triplet; tt=triplet of triplets; q=quartet; br=broad resonance; and m=multiplet. Coupling constants are given in Hertz (Hz). Infrared absorption (IR) spectra were obtained using a Perkin-Elmer 1600 series-FTIR spectrometer. Elemental microanalyses were performed (by Atlantic Microlab Inc., Norcross, Ga.) and gave results for the elements stated within ±0.4% of the theoretical values. Flash column chromatography was performed using Silica Gel 60 (Merck Art 9385). Analytical thin layer chromatography (TLC) was performed using precoated sheets of Silica 60 F$_{254}$ (Merck Art 5719). Melting points (mp) were determined on a Mel-Temp apparatus and are uncorrected. All reactions were performed in septum-sealed flasks under a slight positive pressure of argon, unless otherwise noted. All commercial reagents were used as received from their respective suppliers.

The following abbreviations are used herein: RT denotes room temperature; Et$_2$O refers to diethyl ether: DMF refers to N,N-dimethylformamide; and DMSO refers to dimethylsulfoxide. Other abbreviations include: CH$_3$OH (methanol), EtOH (ethanol), EtOAc (ethyl acetate), DME (ethylene glycol dimethyl ether), Ac (acetyl), Me (methyl), Ph (phenyl), DIEA (N,N-diisopropylethylamine), HOBt (1-hydroxybenzotriazole hydrate), EDC (1-(3-dimethylaminopropyl)-3-ethylcarbarbodiimide hydrochloride), DCC (dicyclohexylcarbodi-imide), and DMAP (4-dimethylaminopyridine).

Unless otherwise indicated, all percentages and ppm are in weight, and all temperatures are in degrees Celsius.

Example 1

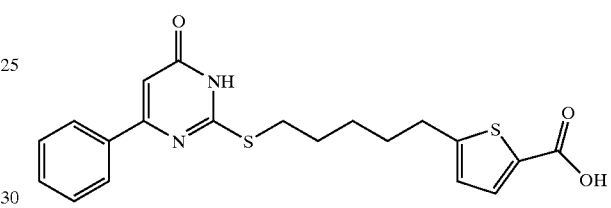

(a) Methyl 5-(5-hydroxy-1-pentynyl)thiophene-2-carboxylate. To a stirred solution of methyl 5-bromothiophene-2-carboxylate (11.05 g, 50 mmol) in diethylamine (150 mL) under an argon atmosphere were added bis(triphenylphosphine)palladium dichloride (175 mg, 0.25 mmol), cuprous iodide (95 mg, 0.5 mmol) and 4-pentyn-1-ol (5.8 mL, 5.24 g, 62 mmol). The resulting mixture was stirred for 18 hours at ambient temperature. After removal of the solvent by concentration in vacuo, the residue obtained was diluted with water (400 mL) and extracted with EtOAc (3×150 mL). The organic extracts were combined, dried over MgSO$_4$, and concentrated in vacuo, to give a brown gum, which was purified by flash chromatography. Elution with hexane:EtOAc (2:1) provided the product as an orange oil (9.89 g, 88% yield). $^1$H NMR (CDCl$_3$) δ: 7.62 (1H, d, J=3.9 Hz), 7.06 (1H, d, J=3.9 Hz), 3.87 (3H, s), 3.80 (2H, t, J=6.1 Hz), 2.58 (2H, t, J=7.0 Hz), 1.87 (2H, tt, J=6.1, 7.0 Hz). Anal. (C$_{11}$H$_{12}$O$_3$S) C, H, S.

(b) Methyl 5-(5-hydroxypentyl)thiophene-2-carboxylate. A suspension of methyl 5-(5-hydroxy-1-pentynyl)thiophene-2-carboxylate (9.25 g, 41.2 mmol) and 5% Pd on carbon (1.39 g, 15% wt. equiv.) in EtOAc (180 mL) was shaken under 50 psi of H$_2$ for 20 hours. The crude reaction mixture was filtered through a pad of Celite, and the filtrate was concentrated in vacuo, to provide the product as a yellow oil (9.33 g, 99% yield). $^1$H NMR (CDCl$_3$) δ: 7.63 (1H, d, J=3.7 Hz), 6.78 (1H, d, J=3.7 Hz), 3.86 (3H, s), 3.65 (2H, t, J=6.5 Hz), 2.85 (2H, t, J=7.5 Hz), 1.78–1.68 (2H, m) 1.65–1.56 (2H, m), 1.49–1.39 (2H, m). Anal. (C$_{11}$H$_{16}$O$_3$S) C, H, S.

(c) Methyl 5-(5-bromopentyl)thiophene-2-carboxylate. A solution of triphenylphosphine (14.43 g, 55 mmol) in 100 mL of CH$_2$C$_2$ was added dropwise to a stirred solution of methyl 5-(5-hydroxypentyl)thiophene-2-carboxylate (10.44 g, 45.7 mmol) and CBr$_4$ (18.24 g, 55 mmol) in CH$_2$Cl$_2$ at about 0° C. over a 15-minute interval. The resulting solution was stirred at 0° C. for about 30 minutes, then overnight at room temperature. The crude reaction mixture was subsequently concentrated in vacuo, and the residue obtained was purified by flash chromatography. Elution with hexane:EtOAc (95:5) provided the product as a yellow oil (12.36 g, 93% yield). $^1$H NMR (CDCl$_3$) δ: 7.63 (1H, d, J=3.7 Hz), 6.79 (1H, d, J=3.7 Hz), 3.86 (3H, s), 3.40 (2H, t, J=6.6 Hz), 2.85 (2H, t, J=7.5 Hz), 1.94–1.84 (2H, m), 1.78–1.67 (2H, m), 1.56–1.47 (2H, m). Anal. (C$_{11}$H$_{15}$O$_2$SBr) C, H, S, Br.

(d) Methyl 5-(5-[(6phenyl-4(3H)-oxopyrimidin-2-yl)thio]pentyl)thiophene-2-carboxylate. To a stirred solution of methyl 5-(5-bromopentyl)thiophene-2-carboxylate (437 mg, 1.5 mmol) in 15 mL of DMF were added 6-phenyl-2-thiouracil (306 mg, 1.5 mmol) and diisopropylethylamine (270 μl, 200 mg, 1.55 mmol). This mixture was heated at about 90° C. under an argon atmosphere for about one hour. After cooling to room temperature, the mixture was poured into water (100 mL). The resulting precipitate was collected by filtration, and then washed with water (2×20 mL) and with ether (2×20 mL), to provide the product as a white solid (474 mg, 76%). $^1$H NMR (DMSO-d$_6$) δ: 12.73 (1H, br), 8.05–8.01 (2H, m), 7.61 (1H, d, J=3.7 Hz), 7.49–7.41 (3H, m), 6.92 (1H, d, J=3.7 Hz), 6.65 (1H, s), 3.77 (3H, s), 3.23 (2H, t, J=7.0 Hz), 2.83 (2H, t, J=7.4 Hz), 1.79–1.62 (4H, m), 1.50–1.41 (2H, m). Anal. (C$_{21}$H$_{22}$N$_2$O$_3$S$_2$) C, H, N, S.

(e) 5-(5-[(6-Phenyl-4(3H)-oxopyrimidin-2-yl)thio]pentyl)thiophene2-carboxylic acid (1). A suspension of methyl 5-(5-[(6-phenyl-4(3H)-oxopyrimidin-2-yl)thio]pentyl)thiophene-2-carboxylate (404 mg, 1 mmol) in 20 mL of 1N NaOH was stirred overnight at ambient temperature, and then filtered. The filtrate was acidified to pH 4.0 by addition of 6N HCl. The precipitate that formed was collected by filtration and washed with water (2×10 mL) to provide the product as a white solid (357 mg, 92% yield). $^1$H NMR (DMSO-d$_6$) δ: 12.76 (2H, br), 8.05–8.01 (2H, m), 7.51–7.41 (4H, m), 6.86 (1H, d, J=3.7 Hz), 6.66 (1H, s), 3.23 (2H, t, J=7.2 Hz), 2.81 (2H, t, J=7.4 Hz), 1.80–1.62 (4H, m), 1.51–1.41 (2H, m). Anal. (C$_{20}$H$_{20}$N$_2$O$_3$S$_2$.1.5 HCl) C, H, N, S.

Example 2

2

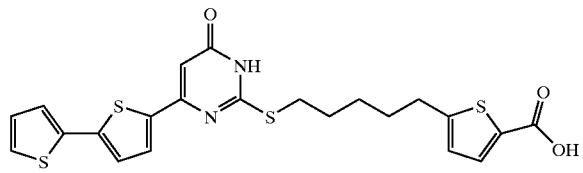

(a) Methyl 5-(3-hydroxypropynyl)thiophene-2-carboxylate. The title compound was prepared by the coupling of methyl 5-bromothiophene-2-carboxylate and propargyl alcohol in a manner analogous to step (a) of Example 1 above. $^1$H NMR (CDCl$_3$) δ: 7.64 (1H, d, J=3.9 Hz), 7.15 (1H, d, J=3.9 Hz), 4.52 (2H, s), 3.88 (3H, s). Anal. (C$_9$H$_8$O$_3$S) C, H, S.

(b) Methyl 5-(3-hydroxypropyl)thiophene-2-carboxylate. The title compound was prepared by the reduction of methyl 5-(3-hydroxypropynyl)thiophene-2-carboxylate in a manner similar to step (b) of Example 1. $^1$H NMR (CDCl$_3$) δ: 7.64 (1H, d, J=3.8 Hz), 6.82 (1H, d, J=3.8 Hz), 3.86 (3H, s), 3.71 (2H, t, J=6.2 Hz), 2.96 (2H, t, J=7.6 Hz), 1.96 (2H, tt, J=6.2, 7.6 Hz). Anal. (C$_9$H$_{12}$O$_3$S) C, H, S.

(c) Methyl 5-(3-bromopropyl)thiophene-2-carboxylate. The title compound was prepared from methyl 5-(3-hydroxypropyl)thiophene-2-carboxylate in a manner analogous to step (c) of Example 1. $^1$H NMR (CDCl$_3$) δ: 7.64 (1H, d, J=3.7 Hz), 6.85 (1H, d, J=3.7 Hz), 3.86 (3H, s), 3.43 (2H, t, J=6.4 Hz), 3.03 (2H, t, J=7.2 Hz), 2.22 (2H, tt, J=6.4, 7.2 Hz). Anal. (C$_9$H$_{11}$O$_2$SBr) C, H, S, Br.

(d) Methyl 5-(3-[(6-phenyl-4(3H)-oxopyrimidin-2-yl)thio]propyl)thiophene-2-carboxylate. The title compound was prepared from 6-phenyl-2-thiouracil and methyl 5-(3-bromopropyl)thiophene-2-carboxylate similar to the method described in step (d) of Example 1. $^1$H NMR (DMSO-d$_6$) δ: 2.10 (2H, m), 3.04 (2H, t, J=7.0 Hz), 3.27 (2H, t, J=7.0 Hz), 3.77 (3H, s), 6.68 (1H, br s), 7.01 (1H, d, J=3.7 Hz), 7.47 (3H, m), 7.64 (1H, d, J=3.7 Hz), 7.98 (2H, d, J=7 Hz).

(e) 5-(3-[(6-Phenyl-4(3H)-oxopyrimidin-2-yl)thio]propyl)thiophene-2-carboxylic acid (2). The title compound was prepared by hydrolysis of methyl 5-(3-[(6-phenyl-4(3H)-oxopyrimidin-2-yl)thio]propyl)thiophene-2-carboxylate in analogy to step (e) of Example 1. $^1$H NMR (DMSO-d$_6$) δ: 2.09 (2H, m), 2.99 (2H, t, J=7.0 Hz), 3.27 (2H, t, J=7.0 Hz), 6.68 (1H, s), 6.95 (1H, d, J=3.7 Hz), 7.47 (4H, m), 7.98 (2H, br s). Anal. (C$_{18}$H$_{16}$N$_2$O$_3$S$_2$.1.0H$_2$O.0.1 NaCl) C, H, N, S.

Example 3

3

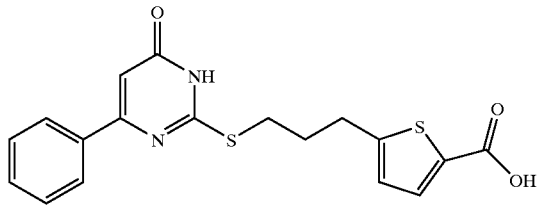

(a) 5-(2-Thienyl)thiophene-2-carboxylic acid. A solution of AgNO$_3$ (8.78 g, 51.7 mmol) in 20 mL of water was added to a vigorously stirred solution of NaOH (4.13 g, 103 mmol) in 20 mL of water. To the resulting slurry was added 2,2'-bisthiophene-5-carboxaldehyde (5.02 g, 25.8 mmol). The reaction mixture was stirred without any external temperature regulation for 2.5 hours, and then filtered. The filtrate was subsequently acidified by addition of concentrated HCl. The precipitate that formed was collected by filtration and washed with water (2×10 mL) to provide the product as a yellow solid (3.64 g, 67% yield). $^1$H NMR (DMSO-d$_6$) δ: 13.17 (1H, br s), 7.65 (1H, d, J=3.9 Hz), 7.62 (1H, dd, J=1.1, 5.2 Hz), 7.48 (1H, dd, J=1.1, 3.7 Hz), 7.34 (1H, d, J=3.9 Hz), 7.13 (1H, dd, J=3.7, 5.2 Hz). Anal. (C$_9$H$_6$O$_2$S$_2$.0.1 H$_2$) C, H, S.

(b) 2-Acetyl-5-(2-thienyl)thiophene. A 1.5M solution of methyllithium in ether (19 mL, 28.5 mmol) was added to a solution of 5-(2-thienyl)thiophene-2-carboxylic acid (2.41 g, 11.5 mmol) in 150 mL of ether at −5° C. under an argon atmosphere. The cooling bath was removed and the reaction was stirred at ambient temperature fir 90 minutes, then poured into 1N HCl (150 mL). The layers were separated and the aqueous phase was extracted with ether (100 mL). The combined organic extracts were washed with saturated NaHCO$_3$ (150 mL), dried over MgSO$_4$, and concentrated in vacuo, to give a green solid, which was purified by flash chromatography. Elution with hexane:EtOAc (85:15) provided the product as a yellow solid (1.89 g, 79% yield). $^1$H NMR (DMSO-d$_6$) δ: 7.89 (1H, d, J=4.0 Hz), 7.64 (1H, dd, J=1.1, 5.1 Hz), 7.52 (1H, dd, J=1.1, 3.7 Hz), 7.42 (1H, d, J=4.0 Hz), 7.14 (1H, dd, J=3.7, 5.1 Hz), 2.52 (3H, s). Anal. (C$_{10}$H$_8$OS$_2$) C, H, S.

(c) Methyl 3-[5-(2-thienyl)thien-2-yl]-3-oxopropionate. A solution of 2-acetyl-5-(2-thienyl)thiophene (1.84 g, 8.8 mmol) in 25 mL of DMF was added under an argon atmosphere to a stirred suspension of 60% NaH in oil (777 mg, 19.4 mmol) in 15 mL of DMF at about 0° C. over a 10-minute interval. The resulting solution was stirred at 0° C. for about 30 minutes preceding addition of dimethylcarbonate (3 mL, 3.21 g, 35.6 mmol). The cooling bath was removed and the reaction was stirred at ambient temperature for 3 hours, and then poured into water (250 mL) and extracted with ether (100 mL). The aqueous layer was subsequently acidified by addition of conc. HCl and extracted with ether (2×100 mL). The combined organic extracts were dried over MgSO$_4$ and concentrated in vacuo, to give a brown gum, which was purified by flash chromatography. Elution with hexane:EtOAc (3:1) provided the product as a yellow solid (2.10 g, $^{89}$% yield). $^1$H NMR (DMSO-d$_6$) δ: 7.96 (1H, d, J=4.0 Hz), 7.69 (1H, dd, J=1.1, 5.1 Hz), 7.56 (1H, dd, J=1.1, 3.7 Hz), 7.46 (1H, d, J=4.0 Hz), 7.16 (1H, dd, J=3.7, 5.1 Hz), 4.13 (2H, s), 3.65 (3H, s). Anal. (C$_{12}$H$_{10}$O$_3$S$_2$) C, H, S.

(d) 6-[5-(2-Thienyl)thien-2-yl]-4(3H)-oxopyrimidine-2-thiol. Thiourea (883 mg, 11.6 mmol) and a solution of methyl 3-[5-(2-thienyl)thien-2-yl]-3-oxopropionate (2.06 g, 7.7 mmol) in ethanol (100 mL) were added sequentially to a 1M solution of sodium ethoxide in ethanol (15 mL). The resulting mixture was heated at reflux under argon for about 24 hours. After removal of the ethanol by concentration in vacuo, the residue was dissolved in water (120 mL). The aqueous layer was acidified by addition of conc. HCl and the precipitate that formed was collected by filtration, and then washed with water (3×30 mL) and with ether (4×30 mL) to provide the product as a yellow solid (1.04 g, 46% yield). $^1$NMR (DMSO-d$_6$) δ: 12.50 (1H, br s), 12.48 (1H, br s), 8.00 (1H, d, J=4.0 Hz), 7.64 (1H, dd, J=1.1, 5.1 Hz), 7.46 (1H, dd, J=1.1, 3.7 Hz), 7.41 (1H, d, J=4.0 Hz), 7.14 (1H, dd, J=3.7, 5.1 Hz), 6.01 (1H, s).

(e) Methyl 5-[5-([6(5-[2-thienyl]thien-2-yl)-4(3H)-oxopyrimidin-2-yl]thio)pentyl]thiophene-2-carboxylate. The title compound was prepared from 6-[5-(2-thienyl)thien-2-yl]-4(3H)-oxopyrimidine-2-thiol and methyl 5-(5-bromopentyl)thiophene-2-carboxylate in a manner similar to Example 1(d). $^1$H NMR (DMSO-d$_6$) δ: 12.68 (1H, br s), 7.82 (1H, d, J=4.0 Hz), 7.57 (1H, d, J=3.8 Hz), 7.56 (1H, dd, J=1.1, 5.1 Hz),7.3 (1H, d, J=4.0 Hz), 7.36 (1H, dd, J=1.1, 3.7 Hz), 7.10 (1H, dd, J=3.7, 5.1 Hz), 6.92 (1H, d, J=38 Hz), 6.60 (1H, s), 3.75 (3H, s), 3.17 (2H, t, J=7.3 Hz), 2.86 (2H, t, J=7.4 Hz), 1.82–1.66 (4H, m), 1.54–1.45 (2H, m). Anal. (C$_{23}$H$_{22}$N$_2$O$_3$S$_4$) C, H, N, S.

(f) 5-[5-([6-(5-[2-Thienyl]thien-2-yl)-4(3H)-oxopyrimidin-2-yl]thio)pentyl]thiophene-2-carboxylic acid (3). The title compound was prepared by hydrolysis of methyl 5-[5-([6-(5-[2-thienyl]thien-2-yl)4(3H)-oxopyrimidin-2-yl]thio)pentyl]thiophene-2-carboxylate in analogy to Example 1(e). $^1$H NMR (DMSO-d$_6$) δ: 12.82 (1H, broad), 7.81 (1H, d, J=4.0 Hz), 7.55 (1H, dd, J=1.1, 5.1 Hz), 7.43 (1H, d, J=3.6 Hz), 7.37 (1H, d, J=4.0 Hz), 7.36 (1H, dd, J=1.1, 3.7 Hz), 7.11 (1H, dd, J=3.7, 5.1 Hz), 6.84 (1H, d, J=3.6 Hz), 6.60 (1H, s), 3.16 (2H, t, J=7.3 Hz), 2.83 (2H, t, J=7.4 Hz), 1.82–1.70 (4H, m), 1.45–1.45 (2H, m). Anal. (C$_{22}$H$_{20}$N$_2$O$_3$S$_4$·1.5 HCl) C, H, N, S.

Example 4

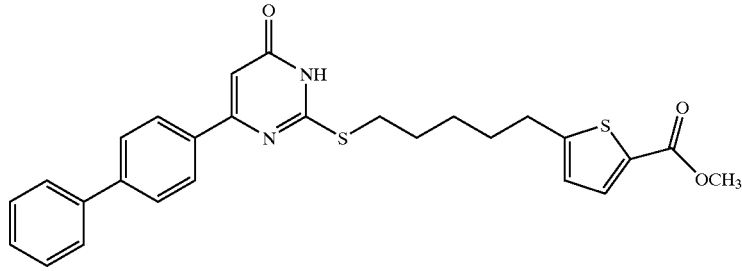

4

(a) Methyl-4-phenylbenzoylacetate. To a stirred suspension of 60% NaH in oil (4.5 g, 112 mmol) in 30 mL of DMF at RT (room temperature) was added dropwise 4-acetylbiphenyl (10 g, 51 mmol) dissolved in 50 mL of DMF. After 30 minutes, the mixture was cooled to 0° C. and dimethylcarbonate (27 mL, 331 mmol) was added neat. The mixture was allowed to warm to RT over a 2-hour period and then poured into 1:1 water/saturated bicarbonate. The aqueous layer was extracted with Et$_2$O, and after removal of the solvent under vacuum, the crude residue was flash chromatographed with 0–40% EtOAc/hexanes to give 12.1 g (94%) of the desired product as a crystalline solid: $^1$H NMR (CDCl$_3$) δ: 3.78 and 3.83 (3H, s), 4.05 and 5.73 (2H, s), 7.38–7.51 (3H, m), 7.62–7.72 (4H, m), 7.83 (1H, d, J=8.5 Hz), 8.03 (2H, d, J=8.6 Hz), 12.53 (0.2H, s).

(b) 6-(4-Biphenylyl)-4(3H)-oxopyrimidine-2-thiol. To a stirred solution of methyl-4-phenylbenzoylacetate (5 g, 19 mmol) and thiourea (2.24 g, 29.5 mmol) in 30 mL of EtOH was added 21% by weight NaOEt in EtOH (15 mL, 41 mmol). The mixture was heated to reflux under argon for 18 hours. After cooling to RT, the suspension was filtered and washed with EtOH and dissolved in water. The solution was acidified with 2N HCl until the pH was 5, and the resulting suspension was filtered, washed with water, and dried to give 2.4 g (43%) of the desired product as a white solid: $^1$H NMR (DMSO-d$_6$) δ: 6.15 (1H, s), 7.41–7.52 (3H, m), 7.72–7.80 (5H, m), 8.00 (1H, d, J=8.1 Hz), 12.51 (1H, d, J=8.0 Hz).

(c) Methyl 5-[5-([6-(4-biphenylyl)-4(3H)-oxopyrimidin-2-yl]thio)pentyl]-thiophene-2-carboxylate (4). The title compound was prepared from 6-(4'-biphenylyl)-4(3H)-oxopyrimidine-2-thiol and methyl 5-(5-bromopentyl)thiophene-2-carboxylate in analogy to Example 1(d). $^1$H NMR (DMSO-d$_6$) δ: 1.50 (2H, m), 1.79 (4H, m), 2.85 (2H, t, J=7.0 Hz), 3.26 (2H, br s), 3.73 (3H, s), 6.70 (1H, br s), 6.93 (1H, d, J=3.7 Hz (3H, m), 7.59 (1H, d, J=3.7 Hz), 7.70–7.75 (5H, m), 8.13 (1H, d, J=8.1 Hz), 12.75 (1H, br s). Anal. (C$_{27}$H$_{26}$N$_2$O$_3$S$_2$) C, H, N, S.

Example 5

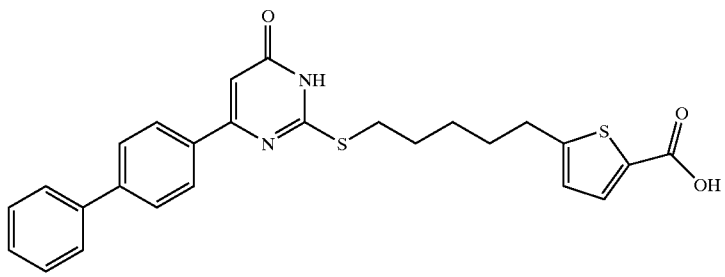

5-[5-([6-(4-Biphenylyl)-4(3H)-oxopyrimidin-2-yl]thio)pentyl]thiophene-2-carboxylic acid (5). The title compound was prepared by hydrolysis of methyl 5-[5-([6-(4'-biphenylyl)-4(3H)-oxopyrimidin-2-yl]thio)pentyl] thiophene-2-carboxylate in analogy to Example 1(e). $^1$H NMR (DMSO-d$_6$) δ: 1.48 (2H, m), 1.67–1.77 (4H, m), 2.83 (2H, t, J=7.0 Hz), 3.25 (2H, br s), 6.72 (1H, s), 6.88 (1H, d, J=3.7 Hz), 7.38–7.51 (3H, m), 7.70–7.76 (6H, m), 8.14 (2H, d, J=8.5 Hz), 12.80 (1H, br s). Anal. (C$_{26}$H$_{24}$N$_2$O$_3$S$_2$.0.7 H$_2$O) C, H, N, S.

Example 6

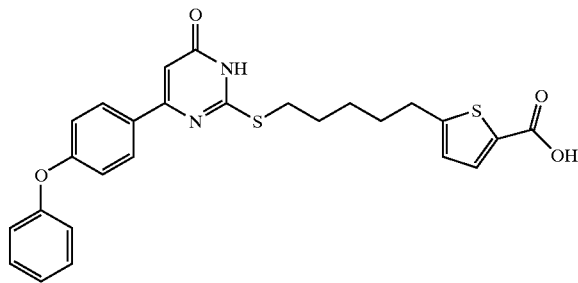

(a) Methyl-4-phenoxybenzoylacetate. The title compound was prepared in a manner as described above in Example 4(a) using 4-phenoxyacetophenone to give the desired product as a yellow solid. $^1$H NMR (CDCl$_3$) δ: 3.69 (3H, s), 3.91 (2H, s), 6.94 (2H, d, J=8.5 Hz), 7.01 (2H, d, J=8.1 Hz), 7.11–7.20 (2H, m), 7.35 (2H, t, J=7.7 Hz), 7.86 (2H, d, J=8.8 Hz).

(b) 6-(4-Phenoxyphenyl)-4(3H)-oxopyrimidine-2-thiol. The title compound was prepared from methyl-4-phenoxybenzoylacetate and thiourea in the manner described in Example 4(b). $^1$H NMR (DMSO-d$_6$) δ: 3.33 (3H, s), 5.97 (1H, s), 6.83–7.19 (5H, m), 7.41 (2H, m), 7.92 (2H, d, J=8.8 Hz), 10.40 (1H, br s).

(c) Methyl 5-[5-([6-(4-phenoxyphenyl)-4(3H)-oxopyrimidin-2-yl]thio)pentyl]-thiophene-2-carboxylate. The title compound was prepared from 6-(4'-phenoxyphenyl)-4(3H)-oxopyrimidine-2-thiol and methyl 5-(5-bromopentyl)thiophene-2-carboxylate in a manner as described in Example 1(d). $^1$H NMR (DMSO-d$_6$) δ: 1.47 (2H, m), 1.72 (4H, m), 2.83 (2H, t, J=7.4 Hz), 3.22 (2H, t, J=7.4 Hz), 3.76 (3H, s), 6.60 (1H, br s), 6.90 (1H, d, J=3.7 Hz), 7.00 (2H, d, J=8.8 Hz), 7.08 (2H, d, J=7.7 Hz), 7.20 (2H, t, J=7.4 Hz), 7.43 (1H, t, J=7.7 Hz), 7.58 (1H, d, J=3.7 Hz), 8.06 (1H, d, J=8.8 Hz), 12.72 (1H, br s). Anal. (C$_{27}$H$_{26}$N$_2$O$_4$S$_2$) C, H, N, S.

(d) 5-[5-([6-(4-Phenoxypheuyl)-4(3H)-oxopyrimidin-2-yl]thio)pentyl]thiophene-2-carboxylic acid (6). The title compound was prepared by hydrolysis of methyl 5-[5-([6-(4'-phenoxyphenyl)-4(3H)-oxopyrimidin-2-yl]thio)pentyl] thiophene-2-carboxylate in a manner like that previously described in Example 1(e). $^1$H NMR (DMSO-d$_6$) δ: 1.44 (2H, m), 1.72 (4H, m), 2.76 (2H, t, J=8.1 Hz), 3.21 (2H, t, J=7.0 Hz), 6.61 (1H, br s), 6.82 (1H, d, J=3.7 Hz), 7.02 (2H, d, J=8.8 Hz) 7.09 (2H, d, J=7.4 Hz), 7.20 (1H, t, J=7.4 Hz), 7.43 (3H, m), 8.06 (2H, d, J=8.8 Hz). Anal. (C$_{26}$H$_{24}$N$_2$O$_4$S$_2$.0.8H$_2$O) C, H, N, S.

Example 7

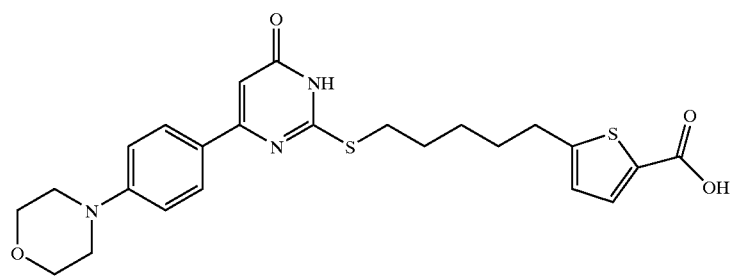

(a) Methyl-4-morpholinylbenzoylacetate. The title compound was prepared as described above in Example 4(b), except using 4-morpholinylacetophenone to give the desired product as a yellow solid. $^1$H NMR (CDCl$_3$) δ: 3.7 (4H, m), 3.78 (3H, s), 3.90 (4H, m), 3.97 (2H, s), 6.92 (2H, d, J=9.2 Hz), 7.91 (2H, d, J=8.8 Hz).

(b) 6(4-Morpholinylphenyl)-4(3H)-oxopyrimidine-2-thiol. The title compound was prepared using the procedure described above in Example 4(b), except using methyl-4-morpholinylbenzoylacetate and thiourea to give the desired product as a light brown solid. $^1$H NMR (DMSO-$d_6$) δ: 3.25 (4H, m), 3.72 (4H, m), 6.01 (1H, s), 6.98 (2H, d, J=9.2 Hz), 7.63 and 7.79 (2H, d, J=8.8 Hz), 12.20 (1H, s), 12.38 (1H, s).

(c) Methyl 5-[5-([6-(4-morpholinylphenyl)-4(3H)-oxopyrimidin-2-yl]thio)pentyl]-thiophene-2-carboxylate. The title compound was prepared from 6-(4'-morpholinylphenyl)-4(3H)-oxopyrimidine-2-thiol and methyl 5-(5-bromopentyl)thiophene-2-carboxylate analogously to Example 1(d). $^1$H NMR (DMSO-$d_6$) δ: 1.50 (2H, m), 1.68 (4H, m), 2.82 (2H, t, J=7.4 Hz), 3.19 (4H, br s), 3.71 (4H, br s), 3.78 (3H, s), 6.48 (1H, br s), 6.93 (3H, m), 7.61 (1H, d, J=4.0 Hz), 7.92 (1H, d, J=9.6 Hz).

(d) 5-[5-([6-(4-Morpholinylphenyl)-4(3H)-oxopyrimidin-2-yl]thio)pentyl]-thiophene-2-carboxylic acid (7). The title compound was prepared by hydrolysis of methyl 5-[5-([6-(4'-morpholinylphenyl)-4(3H)-oxopyrimidin-2-yl]thio)pentyl]thiophene-2-carboxylate as previously described in Example 1(e). $^1$H NMR (DMSO-$d_6$) δ: 1.45 (2H, m), 1.75 (4H, m), 2.83 (2H, t, J=7.0 Hz), 3.20 (4H, m), 3.75 (4H, m), 6.51 (1H, br s), 6.92 (3H, m), 7.54 (1H, d, J=3.7 Hz), 7.93 (2H, d, J=8.8 Hz), 12.68 (2H, br s). Anal. ($C_{24}H_{27}N_3O_4S_2 \cdot 0.9H_2O$) C, H, N, S.

Example 8

(a) 5-Cyano-6-[5-(2-thienyl)thien-2-yl]-4(3H)-oxopyrimidine-2-thiol. To a stirred solution of 2,2'-bisthiophene-5-carboxaldehyde (1.9 g, 10 mmol) in ethanol (50 mL) were added, sequentially, ethyl cyanoacetate (1.13 g, 10 mmol), thiourea (0.76 g, 10 mmol), and $K_2CO_3$ (1.4 g, 10 mmol). The reaction mixture was heated at reflux for 16 hours. After cooling to room temperature, the precipitate was collected by filtration, washed with ethanol (2×20 mL), and then dissolved in warm water (1 L). The aqueous solution was allowed to cool to room temperature, and then acidified to pH 5 by addition of acetic acid. The precipitate that formed was collected by filtration and washed with water (2×20 mL) to provide the product as a yellow solid (1.6 g, 50% yield). $^1$H NMR (DMSO-$d_6$) δ: 12.99 (1H, s), 7.97 (1H, d, J=4.1 Hz), 7.68 (1H, dd, J=1.0, 5.1 Hz), 7.54 (1H, dd, J=1.0, 3.6 Hz), 7.50 (1H, d, J=4.1 Hz), 7.17 (1H, dd, J=3.6, 5.1 Hz).

(b) Methyl 5-[5([5-cyano-6-(5-[2-thienyl]thien-2-yl)-4(3H)-oxopyrimidin-2-yl]thio)pentyl]thiophene-2-carboxylate. The title compound was prepared from 5-cyano-6-[5-(2-thienyl)thien-2-yl]-4(3H)-oxopyrimidine-2-thiol and methyl 5-(5-bromopentyl)thiophene-2-carboxylate in a manner like that previously described in Example 1(d). $^1$H NMR (DMSO-$d_6$) δ: 8.19 (1H, d, J=4.2 Hz), 7.65 (1H, dd, J=1.0, 5.0 Hz), 7.56 (1H, d, J=3.7 Hz), 7.53 (1H, d, J=4.2 Hz), 7.47 (1H, dd, J=1.0, 3.6 Hz), 7.15 (1H, dd, J=3.6, 5.0 Hz), 6.91 (1H, d, J=3.7 Hz), 3.75 (3H, s), 3.23 (2H, t, J=7.4 Hz), 2.86 (2H, t, J=7.3 Hz), 1.84–1.66 (4H, m), 1.57–1.46 (2H, m). Anal. ($C_{24}H_{21}N_3O_3S_4 \cdot 0.33 H_2O$) C, H, N, S.

(c) [5-([5-Cyano-6-(5-[2-thienyl]thien-2-yl)-4(3H)-oxopyrimidin-2-yl]thio)pentyl]thiophene-2-carboxylic acid (8). The title compound was prepared by hydrolysis of methyl 5-[5-([5-cyano-6-(5-[2-thienyl]thien-2-yl)-4(3H)-oxopyrimidin-2-yl]thio)pentyl]thiophene-2-carboxylate in a manner like that described in Example 1(e). $^1$H NMR (DMSO-$d_6$) δ: 8.19 (1H, d, J=4.2 Hz), 7.66 (1H, dd, J=1.0, 5.1 Hz), 7.53 (1H, d, J=4.2 Hz), 7.50 (1H, d, J=3.7 Hz), 7.48 (1H, dd, J=1.0, 3.6 Hz), 7.15 (1H, dd, J=3.6, 5.1 Hz), 6.88 (1H, d, J=3.7 Hz), 3.23 (2H, t, J=7.2 Hz), 2.85 (2H, t, J=7.4 Hz), 1.75–1.56 (4H, m), 1.47–1.36 (2H, m). Anal. ($C_{23}H_{19}N_3O_3S_4 \cdot 0.5 H_2O$) C, H, N, S.

8

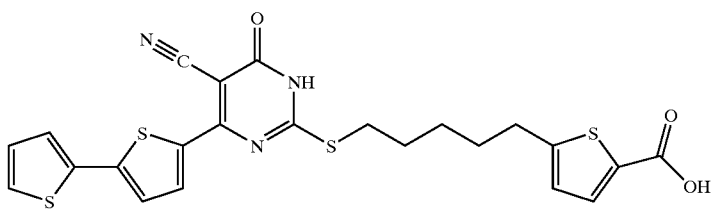

Example 9

9

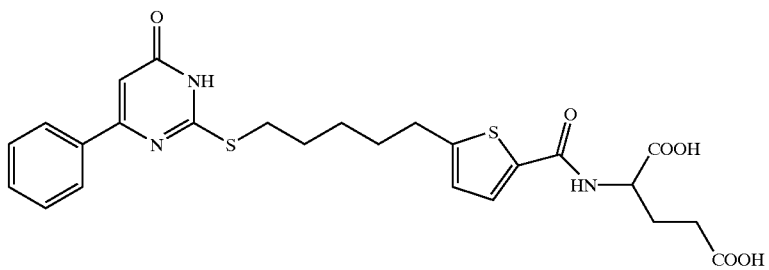

(a) Diethyl N-(5-bromothien-2-yl)glutamate. To a stirred solution of 5-bromothiophene-2-carboxylic acid (15.53 g, 75 mmol), 1-hydroxybenzotriazole (10.81 g, 80 mmol), L-glutamic acid diethyl ester hydrochloride (19.18 g, 80 mmol), and diisopropylethylamine (14 mL, 10.39 g, 80 mmol) in DMF (75 mL) was added 1-(3-dimethylaminopropyl)-3-ethylcarbodiimide hydrochloride (15.34 g, 80 mmol). The resulting solution was stirred under argon at ambient temperature for 18 hours, poured into brine (300 mL), diluted with water (300 mL), and extracted with ether (3×150 mL). The combined organic extracts were washed with water (2×150 mL), dried over $MgSO_4$, and concentrated in vacuo, to give a yellow gum which was purified by flash chromatography. Elution with hexane:EtOAc (2:1) provided the product as a yellow syrup (26.81 g, 91% yield). $^1$H NMR (CDCl$_3$) δ: 7.29 (1H, d, J=3.7 Hz), 7.04 (1H, d, J=3.7 Hz), 6.98 (1H, d, J=7.7 Hz), 4.69 (1H, ddd, J=4.8, 7.7, 12.5 Hz), 4.23 (2H, q, J=7.2 Hz), 4.12 (2H, q, J=7.2 Hz), 2.54–2.37 (2H, m), 2.33–2.22 (1H, m), 2.18–2.04 (1H, m), 1.30 (3H, t, J=7.2 Hz), 1.24 (3H, t, J=7.2 Hz). Anal. ($C_{14}H_{18}NO_5SBr$) C, H, N, S, Br.

(b) Diethyl N-[5-(5-hydroxy-1-pentynyl)theno-2-yl] glutamate. The title compound was prepared from the coupling of diethyl N-(5-bromothien-2-yl)glutamate and 4-pentyn-1-ol as in Example 1(d). $^1$H NMR (CDCl$_3$) δ: 1.2–1.32 (6H, m), 1.84–1.88 (2H, m), 2.1–2.48 (5H, m), 2.57 (2H, t, J=7.00 Hz), 3.80 (2H, t, J=6.25 Hz), 4.11 (2H, q, J=7.00 Hz), 4.22 (2H, q, J=7.00 Hz), 4.7 (1H, m), 6.9 (1H, d, J=5 Hz), 7.04 (1H, d, J=3.68 Hz), 7.37 (1H, d, J=4.1 Hz).

(c) Dietbyl N-[5-(5-hydroxypentyl)theno-2-yl]glutamate. The title compound was prepared by the reduction of diethyl N-[5-(5-hydroxy-1-pentynyl)theno-2-yl]glutamate as previously described in Example 1(e). $^1$H NMR (CDCl$_3$) δ: 1.2–1.32 (6H, m), 1.4–1.77 (10H, m), 2.07–2.54 (5H, m), 2.85 (2H, t, J=7.4 Hz) 3.66 (2H, t, J=6.25 Hz), 4.13 (2H, q, J=7.00 Hz), 4.23 (2H, q, J=7.00 Hz), 4.76 (1H, m), 6.76 (2H, m), 7.38 (1H, d, J=3.3 Hz).

(d) Diethyl N-[5-(5bromopentyl)theno-2-yl]glutamate. The title compound was prepared from diethyl N-[5-(5-hydroxypentyl)theno-2-yl]glutamate like as described in Example 1(c). $^1$H NMR (CDCl$_3$) δ: 1.23–1.35 (6H, m), 1.5–1.94 (10H, m), 2.07–2.53 (5H, m), 2.87 (2H, t, J=7.4 Hz), 3.43 (2H, t, J=6.25 Hz), 4.14 (2H, q, J=7.00 Hz), 4.25 (2H, q, J=7.00 Hz), 4.76 (1H, m), 6.79 (1H, m), 7.40 (1H, d, J=3.68 Hz).

(e) Diethyl N-(5-[5-([6-phenyl-4(3H)-oxopyrimidin-2-yl]thio)pentyl]theno-2-yl)glutamate. The title compound was prepared from 6-phenyl-2-thiouracil and diethyl N-[5-(5-bromopentyl)theno-2-yl]glutarnate in like manner to Example 1(d). $^1$H NMR (DMSO-d$_6$) δ: 1.16 (6H, q, J=7.0 Hz), 1.4–2.2 (10H, m), 2.39 (2H, t, J=8.1 Hz), 2.81 (2H, t, J=8.1 Hz), 3.33 (2H, t, J=6.25 Hz), 4.04–4.18 (4H, m), 4.40 (1H, m), 6.68 (1H, m), 6.86 (1H, t, J=3.4 Hz), 7.46 (3H, br s), 7.67 (1H, d, J=3.4 Hz), 8.03 (2H, br s), 8.61 (1H, d, J=12.78 (1H, br s).

(f) N-(5-[5-([6-Phenyl-4(3H)-oxopyrimidin-2-yl]thio) pentyl]theno-2-yl)glutamic acid (9). The title compound was prepared by hydrolysis of diethyl N-(5-[5-([6-phenyl-4(3H)-oxopyrimidin-2-yl]thio)pentyl]theno-2-yl)glutamate in analogy to Example 1(e). $^1$H NMR (DMSO-d$_6$) δ: 1.4–2.2 (10H, m), 2.33 (2H, t, J=7.3 Hz), 2.81 (2H, t, J=7.0 Hz), 3.23 (2H, t, J=7.0 Hz), 4.31 (1H, m), 6.67 (1H, s), 6.86 (1H, t, J=3.7 Hz), 7.45 (3H, br s), 7.67 (1H, d, J=3.7 Hz), 8.03 (2H, m), 8.48 (1H, d, J=7.7 Hz) 12.60 (3H, br s). Anal. ($C_{25}H_{27}N_3O_6S_2$.0.5$H_2O$) C, H, N, S.

Example 10

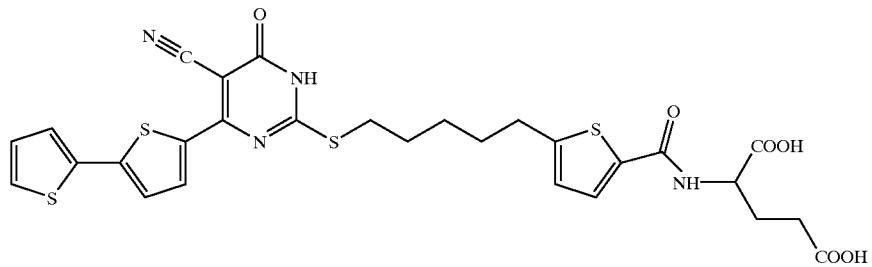

10

(a) Diethyl N-(5-[5-([5-cyano-6-(5-[2-thienyl]thien-2-yl)-4(3H)-oxopyrimidin-2-yl]thio)pentyl]theno-2-yl)glutamate. The title compound was prepared from 5-cyano-6-[5-(2-thienyl)thien-2-yl]-4(3H)-oxopyrimidine-2-thiol and diethyl N-[5-(5-bromopentyl)theno-2-yl]glutamate in analogy to Example 1(d). $^1$H NMR (CDCl$_3$) δ: 8.41 (1H, d, J=4.2 Hz), 7.36 (1H, dd, J=1.1, 5.0 Hz), 7.35 (1H, d, J=3.7 Hz), 7.34 (1H, dd, J=1.1, 3.6 Hz), 7.29 (1H, d, J=4.2 Hz), 7.08 (1H, dd, J=3.6, 5.0 Hz), 6.82 (1H, d , J=6.73 (1H, d, J=3.7 Hz), 4.74 (1H, ddd, J=4.8, 7.8, 11.6 Hz), 4.24 (2H, q, J=7.1 Hz), 4.11 (2H, q, J=7.1 Hz), 3.32 (2H, t, J=7.0 Hz), 2.87 (2H, t, J=7.2 Hz), 2.56–2.24 (3H, m), 2.18–2.08 (1H, m), 1.93–1.72 (4H, m), 1.63–1.52 (2H, m), 1.30 (3H, t, J=7.1 Hz), 1.23 (3H, t, J=7.1 Hz).

(b) N-(5-[5-([5-Cyano-6-(5-[2-thienyl]thien-2-yl)-4(3H)-oxopyrimidin-2-yl]thio)pentyl]theno-2-yl)glutamic acid (10). The title compound was prepared by hydrolysis of diethyl N-(5-[5-([5-cyano-6-(5-[2-thienyl]thien-2-yl)-4 (3H)-oxopyrimidin-2-yl]thio)pentyl]theno-2-yl)glutamate in a manner akin to Example 1(e). $^1$H NMR (DMSO-d$_6$) δ: 8.45 (1H, d , J=7.7 Hz), 8.18 (1H, d, J=4.2 Hz), 7.65 (1H, dd, J=1.1, 5.0 Hz), 7.64 (1H, d, J=3.7 Hz), 7.53 (1H, d, J=4.2 Hz), 7.48 (1H, dd, J=1.1, 3.6 Hz), 7.15 (1H, dd, J=3.6, 5.0 Hz), 6.85 (1H, d, J=3.7 Hz), 4.33 (1H, ddd, J=4.9, 7.7, 9.3 Hz), 3.21 (2H, t, J=7.4 Hz), 2.83 (2H, t, J=7.2 Hz), 2.32 (2H, t, J=7.5 Hz), 2.12–1.89 (2H, m), 1.85–1.66 (4m), 1.57–1.46 (2H, m). Anal. ($C_{28}H_{26}N_4O_6S_4$.1.0 $H_2O$) C, H, N, S.

Example 11

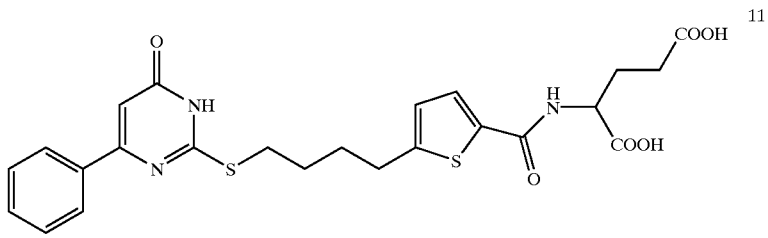

(a) Diethyl N-[5-(4-hydroxy-1-butynyl)theno-2-yl] glutamate. The title compound was prepared from the coupling of diethyl N-(5-bromothien-2-yl)glutamate and 3-butynyl-1-ol as previously described for Example 1(a). $^1$H NMR (CDCl$_3$) δ: 7.38 (1H, d, J=40 Hz), 7.08 (1H, d, J=4.0 Hz), 6.96 (1H, d, J=7.4 Hz), 4.71 (1H, ddd, J=4.8, 7.4, 12.4 Hz), 4.23 (2H, q, J=7.0 Hz), 4.12 (2H, q, J=7.0 Hz), 3.83 (2H, t, J=6.3 Hz), 2.72 (2H, t, J=6.3 Hz), 2.55–2.22 (3H, m), 2.18–2.06 (1H, m), 1.30 (3H, t, J=7.0 Hz), 1.23 (3H, t, J=7.0 Hz). Anal. (C$_{18}$H$_{23}$NO$_6$S) C, H, N, S.

(b) Diethyl N-[5-(4-hydroxybutyl)theno-2-yl]glutamate. The title compound was prepared by the reduction of diethyl N-[5-(4-hydroxy-1-butynyl)theno-2-yl]glutamate as previously described for Example 1(b). $^1$H NMR (CDCl$_3$) δ: 7.39 (1H, d, J=3.7 Hz), 6.77 (1H, d, J=7.7 Hz), 6.76 (1H, d, J=3.7 Hz), 4.73 (1H, ddd, J=5.1, 7.7, 12.1 Hz), 4.23 (2H, q, J=7.0 Hz), 4.11 (2H, q, J=7.0 Hz), 3.68 (2H, t, J=6.4 Hz), 2.87 (2H, t, J=7.3 Hz), 2.53–2.23 (3H, m), 2.17–2.04 (1H, m), 1.83–1.71 (2H, m), 1.68–1.61 (2H, m), 1.30 (3H, t, J=7.0 Hz), 1.23 (3H, t, J=7.0 Hz). Anal. (C$_{18}$H$_{27}$NO$_6$S) C, H, N, S.

(c) Diethyl N-[5-(4-bromobutyl)theno-2-yl]glutamate. The title compound was prepared from diethyl N-[5-(4-hydroxybutyl)theno-2-yl]glutamate as previously described for Example 1(c). $^1$H NMR (CDCl$_3$) δ: 7.39 (1H, d, J=3.7 Hz), 6.79 (1H, d, J=7.7 Hz), 6.77 (1H, d, J=3.7 Hz), 4.73 (1H, ddd, J=4.8, 7.7, 8.1 Hz), 4.23 (2H, q, J=7.0 Hz), 4.11 (2H, q, J=7.0 Hz), 3.42 (2H, t, J=6.3 Hz), 2.86 (2H, t, J=7.5 Hz), 2.53–2.23 (3H, m), 2.17–2.04 (1H, m), 1.95–1.81 (4H, m), 1.30 (3H, t, J=7.0 Hz), 1.23 (3H, t, J=7.0 Hz). Anal. (C$_{18}$H$_{26}$NO$_5$SBr) C, H, N, S, Br.

(d) Diethyl N-(5-[4-([6-phenyl-4(3H)-oxopyrimidin-2-yl]thio)butyl]theno-2-yl)glutamate. The title compound was prepared from 6-phenyl-2-thiouracil and diethyl N-[5-(4-bromobutyl)theno-2-yl]glutamate as described above for Example 1(d). $^1$H NMR (DMSO-d$_6$) δ: 1.16 (6H, m), 1.8–2.2 (8H, m), 2.38 (2H, t, J=8.5 Hz), 2.89 (2H, d, J=8.5 Hz) 3.34 (2H, br s), 4.00–4.13 (4H, m), 4.43 (1H, m), 6.70 (1H, m), 6.87 (1H, t, J=3.7 Hz), 7.48 (3H, br s), 7.66 (1H, d, J=3.7 Hz), 8.03 (2H, br s), 8.60 (1H, d, J=7.6 Hz), 12.80 (1H, br s).

(e) N-(5-[5-([6-Phenyl-4(3H)-oxopyrimidin-2-yl]thio)butyl]thio2-yl)glutamic acid (11). The title compound was prepared by hydrolysis of diethyl N-(5-[4-([$^6$-phenyl-4(3H)-oxopyrimidin-2-yl]thio)butyl]theno-2-yl)glutamate as described above for Example 1(e). $^1$H NMR (DMSO-d$_6$) δ: 1.8–2.2 (8H, m), 2.33 (2H, t, J=6.24 Hz), 2.86 (2H, br s) 3.33 (2H, br s), 4.00–4.13 (4H, m), 4.35 (1H, m), 6.68 (1H, m), 6.87 (1H, t, J=3.7 Hz), 7.49 (3H, br s), 7.66 (1H, d, J=3.7 Hz), 8.03 (2H, br s), 8.49 (1H, d, J=8.1 Hz), 12.60 (3H, br s). Anal. (C$_{24}$H$_{25}$N$_3$O$_6$S$_2$.0.1H$_2$O) C, H, N, S.

Example 12

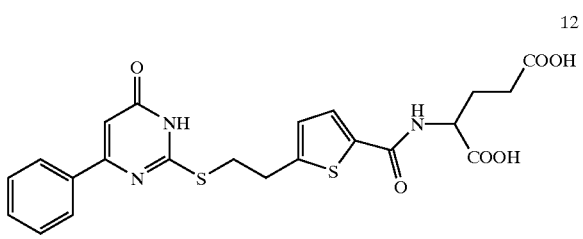

(a) 2-[2-(t-Butyldimethylsilyloxy)ethyl]thiophene. To a stirred solution of 2-(2-thienyl)ethanol (75.26 g, 0.6 mol) in methylene chloride (800 mL) were added t-butyldimethylchlorosilane (97.34 g, 0.6 mol), triethylamine (96 mL, 69.69 g, 0.7 mol) and 4-(dimethylamino) pyridine (1.22 g, 0.01 mol) at 0° C. The cooling bath was removed and the reaction was stirred at ambient temperature overnight. The precipitate (triethylamine hydrochloride) was removed by filtration, and the filtrate was washed sequentially with water (400 mL), 0.5N HCl (400 mL), and brine (400 mL). The aqueous layers were combined and extracted with CH$_2$Cl$_2$(400 mL). The combined organic extracts were dried over MgSO$_4$ and concentrated in vacuo, to provide the product as a yellow oil (139.55 g, 98% yield). $^1$H NMR (CDCl$_3$) δ: 7.13 (1H, d, J=5.1 Hz), 6.92 (1H, dd, J=3.3, 5.1 Hz), 6.83 (1H, d, J=3.3 Hz), 3.82 (2H, t, J=6.7 Hz), 3.03 (2H, t, J=6.7 Hz), 0.89 (9H, s), 0.03 (6H, s). Anal. (C$_{12}$H$_{22}$OSSi) C, H, S.

(b) 5-[2-(t-Butyldimethylsilyloxy)ethyl]thiophene-2-carboxylic acid, dietbyl N-(5-[2-(t-butyldimetlylsilyloxy)ethyl]theno-2-yl)glutamate and diethyl N-[5-(2-hydroxyethyl)theno-2-yl]glutamate. A 2.5M solution of n-butyllitium in hexane (300 mL, 0.75 mol) was added to a solution of 2-[2-(t-butyldimethylsilyloxy)ethyl]thiophene (139.55 g, 0.58 mol) in THF (1L) under an argon atmosphere at –75° C. The resulting reaction mixture was stirred at –75° C. for about an hour, then warmed to –20° C. Dry CO$_2$ was then bubbled through the reaction for 90 minutes. The crude mixture was poured into a mixture of ice (2.5 kg) and saturated NH$_4$Cl (700 mL). The layers were separated, and the aqueous phase was extracted with ether (700 mL) and EtOAc (700 mL). The combined organic extracts were dried over Na$_2$SO$_4$ and concentrated in vacuo, to give an orange solid (180 g), which was used without further purification.

The crude 5-[2-(t-butyldimethylsilyloxy)ethyl]thiophene-2-carboxylic acid was subsequently coupled with L-glutamic acid diethyl ester hydrochloride as described in Example 9(a), to give a brown syrup (200 g), which was used without further purification.

The crude diethyl N-(5-[2-(t-butyldimetlylsilyloxy)ethyl] theno-2-yl)glutamate was dissolved in THF (800 mL) and combined with a 1.0M solution of tetrabutylammonium fluoride (500 mL, 0.5 mol). The resulting solution was stirred at ambient temperature overnight, then poured into water (2 L) and extracted with EtOAc (3×500 mL). The combined organic extracts were washed with brine (600 mL), dried over $Na_2SO_4$ and concentrated in vacuo, to give a brown gum, which was purified by flash chromatography. Elution with hexane:EtOAc (2:1) provided the product as an orange syrup (99.42 g, 48% yield). $^1$H NMR (CDCl$_3$) δ: 7.41 (1H, d, J=3.7 Hz), 6.88 (1H, d, J=7.7 Hz), 6.85 (1H, d, J=3.7 Hz), 4.73 (1H, ddd, J=4.8, 7.7, 12.5 Hz), 4.23 (2H, q, J=7.0 Hz), 4.11 (2H, q, J=7.0 Hz), 3.88 (2H, t, J=6.3 Hz), 3.07 (2H, t, J=6.3 Hz), 2.55–2.23 (3H, m), 2.16–2.02 (1H, m), 1.30 (3H, t, J=7.0 Hz), 1.23 (3H, t, J=7.0 Hz). Anal. ($C_{16}H_{23}NO_6S$) C, H, N, S.

(c) Diethyl N-[5-(2-bromoethyl)theno-2-yl]glutamate. The title compound was prepared from diethyl N-[5-(2-hydroxyethyl)theno-2-yl]glutamate as previously described in Example 1(c). $^1$H NMR (CDCl$_3$) δ: 7.40 (1H, d, J=3.7 Hz), 6.90 (1H, d, J=8.1 Hz), 6.86 (1H, d, J=3.7 Hz), 4.73 (1H, ddd, J=5.1, 8.1, 12.8 Hz), 4.23 (2H, q, J=7.0 Hz), 4.10 (2H, q, J=7.0 Hz), 3.56 (2H, t, J=7.2 Hz), 3.35 (2H, t, J=7.2 Hz), 2.53–2.22 (3H, m), 2.16–2.06 (1H, m), 1.29 (3H, t, J=7.0 Hz), 1.22 (3H, t, J=7.0 Hz). Anal. ($C_{16}H_{22}NO_5SBr$) C, H, N, S, Br.

(d) Diethyl N-(5-[2-([6-phenyl4(3H)-oxopyrimidin-2-yl]thio)ethyl]theno-2-yl)glutamate. The title compound was prepared from 6-phenyl-2-thiouracil and diethyl N-[5-(2-bromoethyl)theno-2-yl]glutamate generally as described in Example 1(d). $^1$H NMR (DMSO-d$_6$) δ: 1.15 (t, 3H, J=7.0 Hz), 1.18 (t, 3H, J=7.0 Hz), 1.97 (m, 2H), 2.41 (t, 2H, J=7.3 Hz), 3.28 (t, partially obscured by $H_2O$, 2H, J=7.3 Hz), 3.50 (t, 2H, J=7.3 Hz), 4.03 (q, 2H, J=7.0 Hz), 4.10 (q, 2H, J=7.0 Hz), 4.35 (m, 1H), 6.70 (s, 1H), 7.00 (d, 1H, J=3.7 Hz), 7.47 (m, 3H), 7.72 (d, 1H, J=3.7 Hz), 8.08 (d, 2H, J=8.1 Hz), 8.67 (d, 1H, J=7.3 Hz), 12.80 (br s, 1H). Anal. ($C_{26}H_{29}N_3O_6S_2$) C, H, N, S.

(e) N-(5-[2-([6-Phenyl-4(3H)-oxopyrimidin-2-yl]thio)ethyl]theno-2-yl)glutamic acid (12). The title compound was prepared by hydrolysis of diethyl N-(5-[2-([6-phenyl-4(3H)-oxopyrimidin-2-yl]thio)ethyl]theno-2-yl)glutamate generally as described in Example 1(e). $^1$H NMR (DMSO-d$_6$) δ: 1.86–2.10 (m, 2H), 2.33 (m, 2H), 3.28 (t, partially obscured by $H_2O$, 2H, J=7.3 Hz), 3.51 (t, 2H, J=7.3 Hz), 4.34 (m, 1H), 6.71 (s, 1H), 6.99 (d, 1H, J=3.3 Hz), 7.47 (m, 3H), 7.72 (d, 1H, J=3.7 Hz), 8.09 (d, 2H, J=7.0 Hz), 8.56 (d, 1H, J=7.7 Hz), 12.6 (br s, 2H). Anal. ($C_{22}H_{21}N_3O_6S_2.0.8H_2O$) C, H, N, S.

Example 13

13

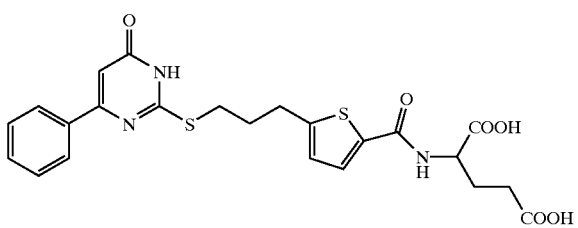

(a) Diethyl N-(5-[3-([6-phenyl-4(3H)-oxopyrimidin-2-yl]thio)propyl]theno-2-yl)glutamate. The title compound was prepared from 6-phenyl-2-thiouracil and diethyl N-[5-(3-bromopropyl)theno-2-yl]glutamate as described above in Example 1(d). $^1$H NMR (DMSO-d$_6$) δ: 1.14 (t, 3H, J=7.0 Hz), 1.16 (t, 3H, J=7.0 Hz), 1.95–2.10 (m, 4H), 2.40 (t, 2H, J=7.3 Hz), 2.97 (t, 2H, J=7.3 Hz), 3.26 (t, 2H, J=7.3 Hz), 4.01 (q, 2H, J=7.0 Hz), 4.08 (q, 2H, J=7.3 Hz), 4.01 (q, 2H, J=7.0 Hz), 4.08 (q, 2H, J=7.0 Hz), 4.36 (m, 1H), 6.67 (s, 1H), 6.94 (d, 1H, J=3.7 Hz), 7.47 (m, 3H), 7.70 (d, 1H, J=3.7 Hz), 7.98 (m, 2H), 8.64 (d, 1H, J=7.7 Hz), 12.75 (br s, 1H). Anal. ($C_{27}H_{31}N_3O_6S_2.0.2H_2O$) C, H, N, S.

(b) N-(5-[3-([6Phenyl-4(3H)-oxopyrimidin-2-yl]thio)propyl]theno-2-yl)glutamic acid (13). The title compound was prepared by hydrolysis of diethyl N-(5-[3-([6-phenyl-4(3H)-oxopyrimidin-2-yl]thio)propyl]theno-2-yl)glutamate as described above in Example 1(e). $^1$H NMR (DMSO-d$_6$) δ: 1.90 (m, 1H), 2.06 (m, 3H), 2.32 (t, 2H, J=7.3 Hz), 2.97 (t, 2H, J=7.3 Hz), 3.27 (t, partially obscured by $H_2O$, 2H, J=7.3 Hz), 4.32 (m, 1H), 6.67 (s, 1H), 6.93 (d, 1H, J=3.7 Hz), 7.47 (m, 3H), 7.70 (d, 1H, J=3.7 Hz), 7.98 (m, 2H), 8.51 (d, 1H, J=7.7 Hz), 12.60 (br s, 2H). Anal. ($C_{23}H_{23}N_3O_6S_2.0.5H_2O$) C, H, N, S.

Example 14

14

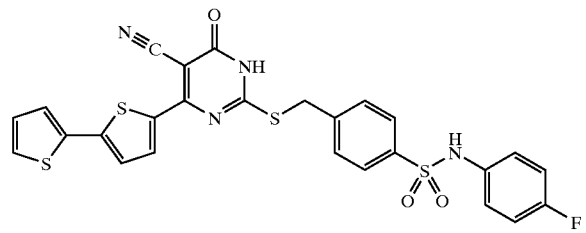

N-(4-Fluorophenyl) 4-[([5-cyano-6-(5-[2-thienyl]thien-2-yl)-4(3H)-oxopyrimidin-2-yl]thio) methyl] benzenesulfonamide (14). The title compound was prepared from 5-cyano-6-[5-(2-thienyl)thien-2-yl]-4(3H)-oxopyrimidine-2-thiol and N-(4-fluorophenyl) 4-(bromomethyl) benzenesulfonamide generally as described in Example 1(d). $^1$H NMR (DMSO-d$_6$) δ: 4.44 (s, 2H), 7.01–7.13 (m, 5H), 7.43–7.64 (m, 8H), 8.07 (d, 1H, J=3.7 Hz), 10.21 (s, 1H), 13.8 (br s, 1H). Anal. ($C_{26}H_{17}N_4O_3S_4F.1.4H_2O$) C, H, N.

Example 15

15

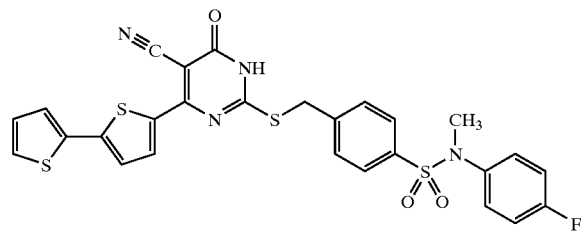

(a) (4-Fluorophenyl)methylamine. A stirred solution of 4-fluoroaniline (5.01 g, 45.1 mmol), methyliodide (3.09 mL, 49.60 mmol) and N,N-diisopropylethylamine (9.4 mL, 54.10 mmol) in 50 mL of DMF was heated at 70° C. for 1 hour. The cooled reaction mixture was poured into $H_2O$ and extracted with EtOAc (2 times). The combined organic layer was washed with saturated NaCl solution (3×), dried over MgSO$_4$, and concentrated at reduced pressure. After chromatography on silica (7:1 hexanes/EtOAc), the title compound was isolated as an amber liquid (46%). $^1$H NMR (CDCl$_3$) δ: 2.85 (s, 3H), 6.77 (m, 2H), 6.95 (m, 2H). Anal. ($C_7H_8NF$) C, H, N.

(b) N-(4-Fluorophenyl)-N-methyl 4-(bromomethyl) benzenesulfonamide. To a stirred solution of (4-fluorophenyl)methylamine (0.42 g, 3.36 mmol) and N,N- diisopropylethylamine (0.64 mL, 3.69 mmol) in 20 mL of CH₂Cl₂ was added 4-(bromomethyl)benzenesulfonyl chloride (0.905 g, 3.36 mmol). After 1 hour at RT the reaction mixture was poured into 0.5N HCl and extracted with CH₂Cl₂ (2×). The combined organic layers were washed with saturated NaCl solution, dried over MgSO₄ and the solvent removed under reduced pressure. After chromatography on silica (5:1 hexanes/EtOAc), the title compound was isolated as an oil, which solidified on standing (76%). ¹H NMR(CDCl₃) δ: 3.16 (s, 3H), 4.49 (s, 2H), 7.04 (m, 4H), 7.50 (m, 4H).

(c) N-(4-Fluorophenyl)-N-methyl 4-[([5cyano-6-(5-[2-thienyl]thien-2-yl)-4(3H)-oxopyrimidin-2-yl]thio)methyl]benzenesulfonamide (15). The title compound was prepared from 5-cyano-6-[5-(2-thienyl)thien-2-yl]-4(3H)-oxopyrimidine-2-thiol and N-(4-fluorophenyl)-N-methyl 4-(bromomethyl)benzenesulfonamide as in Example 1(d). ¹H NMR (DMSO-d₆) δ: 3.04 (s, 3H), 4.61 (s, 2H), 7.05 (m, 4H), 7.14 (m, 2H), 7.49 (m, 4H), 7.65 (d, 1H, J=5.2 Hz), 7.69 (d, 2H, J=8.1 Hz), 8.17 (d, 1H, J=3.7 Hz). Anal. (C₂₇H₁₉N₄O₃S₄F.1.6H₂O) C, H, N, S.

Example 16

(a) Methyl 4-amino-3-methylbenzoate. To a solution of 3-methyl-4-nitrobenzoic acid (6.50 g, 33.3 mmol) in 100 mL of MeOH was added 700 mg of 5% Pd/C. The mixture was hydrogenated at 48 psi H₂ for 24 hours, the catalyst was removed by suction filtration, and the filtrate was concentrated under reduced pressure. The title compound was obtained as a white solid (99%). ¹H NMR (CDCl₃) δ: 2.19 (s, 3H), 3.85 (s, 3H), 4.20 (br s, 2H), 6.65 (d, 2H, J=8.1 Hz), 7.72 (d, 2H, J=8.1 Hz), 7.76 (s, 1H). Anal. (C₉H₁₁NO₂) C, H, N.

(b) Methyl 4-(chlorosulfonyl)-3-methylbenzoate. The procedure described in *Chem. Ber.* 90 (1957), 841, was used to convert methyl 4-amino-3-methylbenzoate to the title sulfonyl chloride in 56% yield. ¹H NMR (CDCl₃) δ: 2.84 (s, 3H), 3.98 (s, 3H), 8.07 (d, 1H, J=8.1 Hz), 8.08 (s, 1H), 8.14 (d, 1H, J=8.1 Hz). Anal. (C₉H₉O₄SCl) C, H, S, Cl.

(c) N-(4-Fluorophenyl) 4-(carbomethoxy)-2-methylbenzenesulfonamide. The title compound was prepared from 4-fluoroaniline and methyl 4-(chlorosulfonyl)-3-methylbenzoate as previously described in Example 15(b). ¹H NMR (CDCl₃) δ: 2.68 (s, 3H), 3.93 (s, 3H), 6.62 (s, 1H), 6.95 (m, 3H), 7.93 (m, 3H). Anal. (C₁₅H₁₄NO₄SF) C, H, N, S.

16

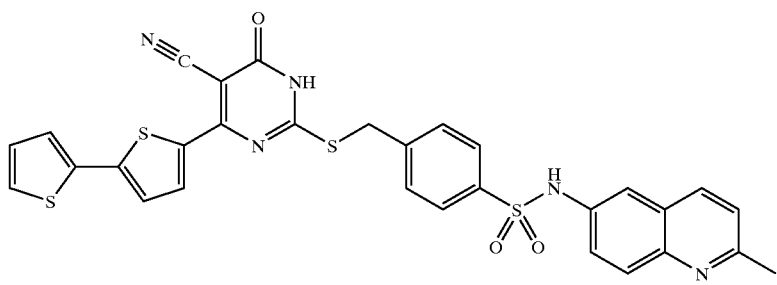

N-(2-Methylquinolin-6-yl) 4-[([5-cyan-6-(5-[2-thienyl]thien-2yl)-4(3H)-oxopyrimidin-2-yl]thio)methyl]benzenesulfonamide (16). The title compound was prepared from 5-cyano-6-[5-(2-thienyl)thien-2-yl]-4(3H)-oxopyrimidine-2-thiol and N-(2-methylquinolin-6-yl) 4-(bromomethyl)benzenesulfonamide as in Example 1(d). ¹H NMR (DMSO-d₆) δ: 2.56 (s, 3H), 4.28 (s, 2H), 7.10 (d, 1H, J=3.7 Hz with fine splitting), 7.30 (d, 1H, J=8.5 Hz), 7.35 (d, 1H, J=4.0 Hz), 7.40–7.58 (m, 6H), 7.71 (d, 2H, J=8.5 Hz), 7.76 (d, 1H, J=9.2 Hz), 7.98 (d, 1H, J=4.0 Hz), 8.08 (d, 1H, J=8.5 Hz), 10.58 (s, 1H). Anal. (C₃₀H₂₁N₅O₃S₄.0.3CH₂Cl₂.1.4H₂O) C, H, N, S.

Example 17

(d) N-4-Fluorophenyl) 4-(hydroxymethyl)-2-methylbenzenesulfonamide. To an ice-cold, stirred solution of N-(4-fluorophenyl) 4-(carboxymethyl)-3-methylbenzoate (1.00 g, 3.09 mmol) in 25 mL THF was added diisobutyl aluminum hydride (7 mL, 1.5 M solution in toluene, 10.5 mol). After 30 minutes at 0° C., another 7 mL of diisobutyl aluminum hydride was added. When starting material was gone, the reaction was quenched with saturated Rochelle salt, diluted with EtOAc and stirred vigorously until layers separated. The organic layer was washed with saturated NaCl solution, dried over MgSO₄, and the solvents removed under reduced pressure. The residue was purified by chromatography on silica (gradient 20:1 to 5:1 CH₂Cl₂/EtOAc). The title compound was iso-

17

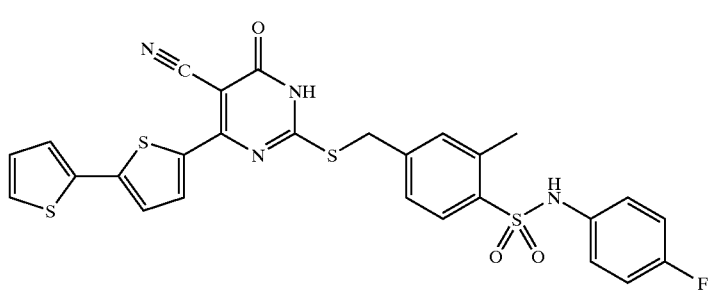

lated as a colorless oil, which solidified on standing (798 mg, 87%). ¹H NMR (CDCl₃) δ: 2.63 (s, 3H), 4.73 (s, 2H), 6.57 (s, 1H), 6.94 (m, 4H), 7.24 (d, 1H, J=8.1 Hz), 7.30 (s, 1H), 7.86 (d, 1H, J=8.1 Hz). Anal. (C₁₄H₁₄NO₃SF) C, H, N, S.

(e) N-(4-Fluorophenyl) 4-(bromomethyl)-2-methylbenzenesulfonamide. The title compound was prepared from N-(4-fluorophenyl) 4-(hydroxymethyl)-2-methylbenzenesulfonamide in the manner described in Example 1(c). ¹H NMR (CDCl₃) δ: 2.62 (s, 3H), 4.42 (s, 2H), 6.55 (s, 1H), 6.89–7.01 (m, 4H), 7.30 (d, 2H, J=8.1 Hz), 7.84 (d, 1H, J=8.1 Hz). Anal. (C₁₄H₁₃NO₂SBrF) C, H, N, S, Br.

(f) N-(4-Fluorophenyl) 4-[([5-cyano-6-(5-[2-thienyl]thien-2-yl)-4(3H)-oxopyrimidin-2-yl]thio) methyl]-2-methylbenzenesulfonamide (17). The title compound was prepared from 5-cyano-6-[5-(2-thienyl)thien-2-yl]-4(3H)-oxopyrimidine-2-thiol and N-(4-fluorophenyl) 4-(bromomethyl)-2-methylbenzenesulfonamide as described in Example 1(d). ¹H NMR (DMSO-d₆) δ: 2.52 (s, 3H), 4.45 (s, 2H), 6.99 (m, 4H), 7.15 (t, 1H, J=4.8 Hz), 7.46 (m, 4H), 7.65 (d, 1H, J=4.8 Hz), 7.76 (d, 1H, J=8.1 Hz), 8.12 (d, 1H, J=3.7 Hz), 10.32 (s, 1H). Anal. (C₂₇H₁₉N₄O₃SF.1.1H₂O.0.5EtOAc) C, H, N, S.

Example 18

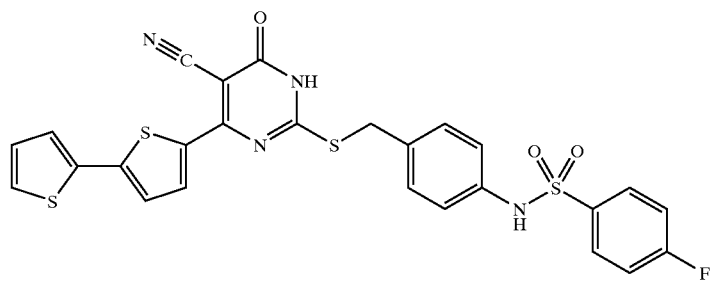

18

(a) N-[4-(Carbomethoxy)phenyl] 4-fluorobenzenesulfonamide. To a stirred solution of methyl 4-aminobenzoate (1.5 g, 9.9 mmol) and pyridine (0.8 mL, 9.9 mmol) in CH₂Cl₂ was added 4-fluorobenzenesulfonyl chloride (1.93 g, 9.9 mmol). After stirring overnight at RT, the reaction mixture was diluted with CH₂Cl₂, and washed sequentially with 0.5N HCl, saturated NaHCO₃ solution, and saturated NaCl solution, dried over MgSO₄, and concentrated under reduced pressure. The residue was purified by chromatography on silica (CH₂Cl₂) to give the title compound as a pale yellow solid (2.42 g, 79%). ¹H NMR (CDCl₃) δ: 3.88 (s, 3H), 7.13 (m, 5H), 7.84 (dd, 2H, J=9.0, 5.1 Hz), 7.93 (d, 2H, J=8.8 Hz). Anal. (C₁₄H₁₂NO₄SF) C, H, N, S.

(b) N-[4-(Hydroxymethyl)phenyl] 4-fluorobenzenesulfonamide. The title compound was prepared by the reduction of N-[4-(carbomethoxy)phenyl] (4-fluorophenyl)benzenesulfonamide as generally described in Example 17(d). ¹H NMR (CDCl₃) δ: 4.62 (s, 2H), 7.03 (br s, 1H), 7.08 (m, 4H), 7.24 (d, 2H, J=8.5 Hz), 7.77 (dd, 2H, J=8.8, 5.1 Hz).

(c) N-(4-[([5-Cyano-6-(5-[2-thienyl]thien-2-yl)-4(3H)-oxopyrimidin-2-yl]thio) methyl]phenyl) 4-fluorobenzenesulfonamide (18). The title compound was prepared from 5-cyano-6-[5-(2-thienyl)thien-2-yl]-4(3H)-oxopyrimidine-2-thiol and N-[4-(bromomethyl)phenyl] 4-fluorobenzenesulfonamide as in Example 1(d). ¹H NMR (DMSO-d₆) δ: 4.36 (s, 2H), 7.02 (d, 2H, J=8.5 Hz), 7.14 (t, 1H, J=3.7 Hz), 7.73 (m, 4H), 7.48 (m, 2H), 7.64 (d, 1H, J=4.8 Hz), 7.73 (dd, 2H, J=9.2, 5.1 Hz), 8.13 (d, 1H, J=3.7 Hz), 10.32 (s, 1H). Anal. (C₂₆H₂₇N₄O₃S₄F.0.6EtOAc.0.8H₂O) C, H, N, S.

Example 19

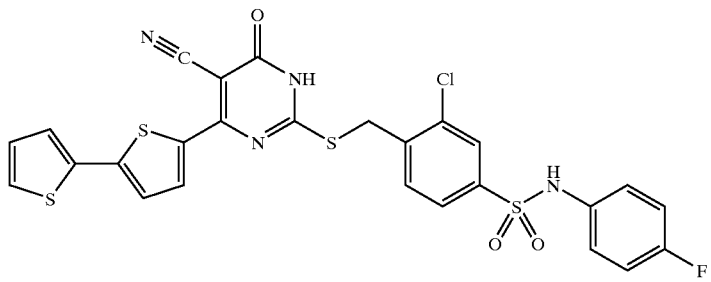

19

(a) Methyl 4-amino-2-chlorobenzoate. A solution of methyl 2-chloro-4-nitrobenzoate (4.5 g, 20.9 mmol) and tin (II) chloride dihydrate (18.84 g, 83.5 mmol) in 100 mL EtOAc was heated cautiously to 70° C. for 30 minutes. After cooling, the reaction mixture was diluted with EtOAc and washed with H₂O (2×), then with saturated NaCl solution, dried over MgSO₄ and concentrated under reduced pressure. In this manner, the title compound was isolated as an off-while solid (99%). ¹H NMR (CDCl₃) δ: 3.86 (s, 3H), 4.10 (br s, 2H), 6.53 (d, 1H, J=8.5 Hz with fine splitting), 6.70 (s, 1H, with fine splitting), 7.78 (d, 1H, J=8.5 Hz). Anal. ($C_8H_8NO_2Cl$) C, H, N, Cl.

(b) Methyl 4-(chlorosulfonyl)-2-chlorobenzoate. The procedure described in *Chem. Ber.* 90 (1957), 841, was used to convert methyl 4-amino-2-chlorobenzoate to the title sulfonyl chloride in quantitative yield. ¹H NMR (CDCl₃) δ: 4.00 (s, 3H), 8.00 (AB, 2H, J=8.1 Hz), 8.13 (s, 1H, with fine splitting). Anal. ($C_8H_8O_4SCl$) C, H, S, Cl.

(c) N-(4-Fluorophenyl) 4-(carbomethoxy)-3-chlorobenzenesulfonamide. The title compound was prepared from 4-fluoroaniline and methyl 4-(chlorosulfonyl)-2-chlorobenzoate in the manner described in Example 15(b). ¹H NMR (CDCl₃) δ: 3.95 (s, 3H), 6.63 (s, 1H), 6.95–7.08 (m, 4H), 7.58 (d, 1H J=8.5 Hz, with fine splitting), 7.81 (s, 1H, with fine splitting), 7.84 (d, 1H, J=8.1 Hz). Anal. ($C_{14}H_{11}NO_4SClF$) C, H, N, S, Cl.

(d) N-(4-Fluorophenyl) 4-(hydroxymethyl)-3-chlorobenzenesulfonamide. The title compound was prepared by the reduction of N-(4-fluorophenyl) 4-(carbomethoxy)-3-chlorobenzenesulfonamide as described in Example 17(d). ¹H NMR (CDCl₃) δ: 4.82 (s, 2H), 6.51 (s, 1H), 6.94–7.07 (m, 4H), 7.61 (AB, 2H, J=8.1 Hz, with fine splitting), 7.71 (s, 2H, with fine splitting). Anal. ($C_{13}H_{11}NO_3SClF$) C, H, N, S, Cl.

(e) N-(4-Fluorophenyl) 4-(bromomethyl)-3-chlorobenzenesulfonamide. The title compound was prepared from N-(4-fluorophenyl) 4-(hydroxymethyl)-3-chlorobenzenesulfonamide as described in Example 1(c). ¹H NMR (CDCl₃) δ: 4.54 (s, 2H), 6.66 (s, 1H), 6.95–7.09 (m, 4H), 7.53 (AB, 2H, J=8.1 Hz, with fine splitting), 7.77 (s, 1H with fine splitting). Anal. ($C_{13}H_{10}NO_2SBrCl$) C, H, N, S, Br, Cl.

(f) N-(4-Fluorophenyl) 4-[([5-cyano-6-(5-[2-thienyl]thien-2-yl)-4(3H)-oxopyrimidin-2-yl]thio)methyl]-3-chlorobenzenesulfonamide (19). The title compound was prepared from 5-cyano-6-[5-(2-thienyl)thien-2-yl]-4(3H)-oxopyrimidine-2-thiol and N-(4-fluorophenyl) 4-(bromomethyl)-3-chlorobenzenesulfonamide as described in Example 1(d). ¹H NMR (DMSO-d₆) δ: 4.48 (s, 2H), 7.02 (m, 4H), 7.13 (t, 1H, J=3.7 Hz), 7.42 (m, 2H), 7.59 (m, 2H), 7.76 (s, 1H, with fine splitting), 7.80 (d, 1H, J=8.1 Hz), 8.04 (d, 1H, J=4.0 Hz), 10.32 (s, 1H). Anal. ($C_{26}H_{16}N_4O_3S_4ClF \cdot 1.5H_2O$) C, H, N, S, Cl.

Example 20

(a) N-[4-(Carbomethoxy)phenyl]-N-methyl 4-fluorobenzenesulfonamide. A stirred solution of N-[4-(carbomethoxy)phenyl] 4-fluorobenzenesulfonamide (440 mg, 1.42 mmol), methyl iodide (0.132 mL, 2.13 mmol), and N,N-diisopropylethylamine (0.372 mL, 2.13 mmol) in CH₂Cl₂ was heated at reflux for 18 hours. Another 0.10 mL of methyl iodide and 0.2 mL of N,N-diisopropylethylamine were added, and heating continued for 4 hours more. After cooling, the mixture was diluted with EtOAc and washed sequentially with 0.5N HCl, then saturated NaCl solution. The organic layer was separated, dried over MgSO₄ and the solvent removed under reduced pressure. The residue was purified by chromatography on silica (CH₂Cl₂) to give the title compound (386 mg, 84%) as a white solid. ¹H NMR (CDCl₃) δ: 3.20 (s, 3H), 3.95 (s, 3H), 7.12 (dd, 2H, J=8.8, 8.5 Hz), 7.21 (d, 2H, J=8.8 Hz), 7.53 (dd, 2H, J=8.8, 5.1 Hz), 7.98 (d, 2H, J=8.8 Hz). Anal. ($C_{15}H_{14}NO_4SF$) C, H, N, S.

(b) N-[4-(Hydroxymethyl)phenyl]-N-methyl 4-fluorobenzenesulfonamide. The title compound was prepared by the reduction of N-[4-(carbomethoxy)phenyl]-N-methyl 4-fluorobenzenesulfonamide as described in Example 17(d). ¹H NMR (CDCl₃) δ: 3.17 (s, 3H), 4.70 (s, 2H), 7.09 (d, 2H, J=8.5 Hz), 7.15 (d, 2H, J=8.5 Hz), 7.32 (d, 2H, J=8.5 Hz), 7.56 (dd, 2H, J=9.1, 5.1 Hz).

(c) N-[4-(Bromomethyl)phenyl]-N-methyl 4-fluorobenzenesulfonamide. The title compound was prepared from N-[4-(hydroxymethyl)phenyl]-N-methyl 4-fluorobenzenesulfonamide as described in Example 1(c). ¹H NMR (CDCl₃) δ: 3.16 (s, 3H), 4.47 (s, 2H), 7.08 (d, 2H, J=8.5 Hz), 7.14 (dd, 2H, J=8.8, 8.5 Hz), 7.31 (d, 2H, J=8.5 Hz), 7.55 (dd, 2H, J=8.8, 5.1 Hz). Anal. ($C_{14}H_{13}NO_2SBrF$) C, H, N, S, Br.

(d) N-(4-[([5Cyano-6(5-[2-thienyl]thien-2-yl)-4(3H)-oxopyrimidin-2-yl]thio)methyl]phenyl)-N-methyl 4-fluorobenzenesulfonamide (20). The title compound was prepared from 5-cyano-6-[5-(2-thienyl)thien-2-yl]-4(3H)-oxopyrimidine-2-thiol and N-[4-(bromomethyl)phenyl]-N-methyl 4-fluorobenzenesulfonamide as described in Example 1(d). ¹H NMR (DMSO-d₆) δ: 3.08 (s, 3H), 4.53 (s, 2H), 7.07 (d, 2H, J=8.5 Hz), 7.15 (t, 1H, J=3.7 Hz), 7.35 (dd, 2H, J=8.8, 8.8 Hz), 7.45 (d, 2H, J=8.5 Hz), 7.53 (m, 4H), 7.66 (d, 1H, J=4.0 Hz), 8.19 (d, 1H, J=4.1 Hz). Anal. ($C_{27}H_{19}N_4O_3S_4F \cdot 0.5H_2O$) C, H, N, S.

20

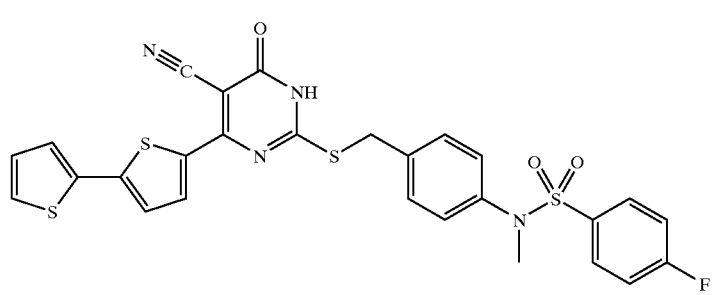

Example 21

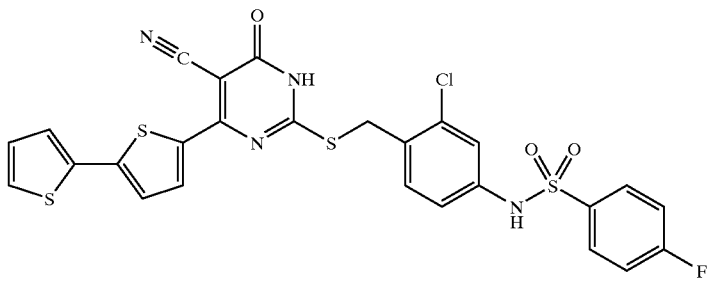

21

(a) N-[4-(Carbomethoxy)-3-chlorophenyl] 4-fluorobenzenesulfonamide. The title compound was prepared from methyl 4-amino-2-chlorobenzoate and 4-fluorobenzenesulfonyl chloride as previously described in Example 15(b). $^1$H NMR (CDCl$_3$) δ: 3.89 (s, 3H), 7.05 (dd, 1H, J=8.5, 2.2 Hz), 7.14–7.20 (m, 3H), 7.78 (d, 1H, J=8.5 Hz), 7.87 (dd, 2H, J=7.0, 5.0 Hz). Anal. (C$_{14}$H$_{11}$NO$_4$SClF) C, H, N, S, Cl.

(b) N-[3-Chloro-4-(hydroxymethyl)phenyl] 4-fluorobenzenesulfonamide. The title compound was prepared by the reduction of N-[4-(carbomethoxy)-3-chlorophenyl] 4-fluorobenzenesulfonamide as described in Example 17(c). $^1$H NMR (CDCl$_3$) δ: 4.70 (s, 2H), 6.97 (d, 1H, J=8.5 Hz), 7.05 (s, 1H), 7.14 (m, 3H), 7.35 (d, 1H, J=8.5 Hz), 7.81 (dd, 2H, J=8.8, 5.1 Hz). Anal. (C$_{13}$H$_{11}$NO$_3$SClF) C, H, N, S, Cl.

(c) N-(3-Chloro-4-[([5-cyano-6-(5-[2-thienyl]thien-2-yl)-4(3H)-oxopyrimidin-2-yl]thio)methyl]phenyl) 4-fluorobenzenesulfonamide (21). The title compound was prepared from 5-cyano-6-[5-(2-thienyl)thien-2-yl]-4(3H)-oxopyrimidine-2-thiol and N-[4-(bromomethyl)-3-chlorophenyl] 4-fluorobenzenesulfonamide as described in Example 1(d). $^1$H NMR (DMSO-d$_6$) δ: 4.42 (s, 2H), 7.01 (d, 1H, J=8.1 Hz), 7.16 (m, 2H), 7.33 (dd, 2H, J=8.8, 8.8 Hz), 7.49 (m, 3H), 7.64 (d, 1H, J=4.8 Hz), 7.80 (dd, 2H, J=8:9, 5.1 Hz), 8.10 (d, 1H, J=4.1 Hz), 10.62 (s, 1H). Anal. (C$_{26}$H$_{16}$N$_4$O$_3$S$_4$ClF.0.5H$_2$O) C, H, N, S.

Example 22

(a) N-[4-(Carbomethoxy)-2-methylphenyl] 4-fluorobenzenesulfonamide. The title compound was prepared from methyl 4-amino-3-methylbenzoate and 4-fluorobenzenesulfonyl chloride in the manner earlier described in Example 15(b). $^1$H NMR (CDCl$_3$) δ: 2.08 (s, 3H), 3.92 (s, 3H), 6.61 (s, 1H), 7.13 (dd, 2H, J=8.5, 8.5 Hz), 7.46 (d, 1H, J=8.1 Hz), 7.81 (m, 4H). Anal. (C$_{15}$H$_{14}$NO$_4$SF) C, H, N, S.

(b) N-[4-(Hydroxymethyl)-2-methylphenyl] 4-fluorobenzenesulfonamide. The title compound was prepared by the reduction of N-[4(carbomethoxy)-2-methylphenyl] 4-fluorobenzenesulfonamide as described above in Example 17(d). $^1$H NMR (CDCl$_3$) δ: 2.01 (s, 3H), 4.62 (s, 2H), 6.37 (s, 1H), 7.13 (m, 3H), 7.25 (dd, 2H, J=8.1, 5.8 Hz), 7.73 (dd, 2H, J=8.8, 5.1 Hz). Anal. (C$_{14}$H$_{14}$NO$_3$SF.0.1H$_2$O) C, H, N, S.

(c) N-(4-[([5-Cyano-6-(5-[2-thienyl]thien-2-yl)4(3H)-oxopyrimidin-2-yl]thio)methyl]-2-methylphenyl) 4-fluorobenzenesulfonamide (22). The title compound was prepared from 5-cyano-6-[5-(2-thienyl)thien-2-yl]-4(3H)-oxopyrimidine-2-thiol and N-[4-(bromomethyl)-2-methylphenyl] 4-fluorobenzenesulfonamide as described in Example 1(d). $^1$H NMR (DMSO-d$_6$) δ: 1.95 (s, 3H), 4.44 (s, 2H), 6.89 (d, 1H, J=8.1 Hz), 7.19 (m, 3H), 7.31 (s, 1H), 7.35 (d, 2H, J=8.8 Hz), 7.53 (d, 2H, J=3.7 Hz), 7.67 (dd, 2H, J=8.8, 5.1 Hz), 8.19 (d, 1H, J=4.1 Hz), 9.63 (s, 1H). Anal. (C$_{27}$H$_{19}$N$_4$O$_3$S$_4$F.0.5H$_2$O) C, H, N, S.

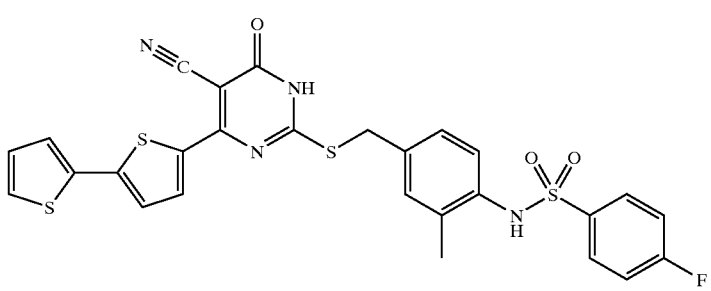

22

Example 23

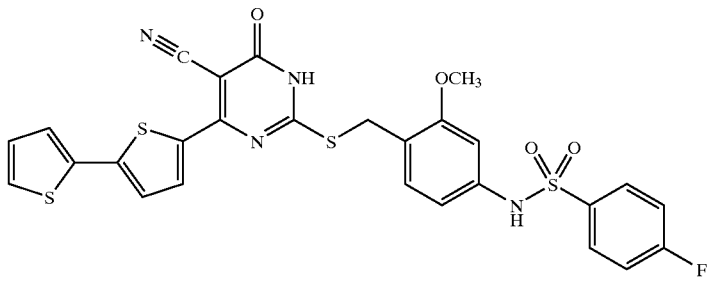

(a) N-[4-(Carbomethoxy)-3-methylphenyl] 4-fluorobenzenesulfonamide. The title compound was prepared from methyl 4-amino-2-methylbenzoate and 4-fluorobenzenesulfonyl chloride as described in Example 15(b). $^1$H NMR (CDCl$_3$) δ: 3.84 (s, 3H), 3.85 (s, 3H), 6.57 (d, 1H, J=8.5 Hz with fine splitting), 6.82 (s, 1H, with fine splitting), 6.91 (s, 1H), 7.14 (dd, 2H, J=8.8, 8.5 Hz), 7.71 (d, 1H, J=8.5 Hz), 7.84 (dd, 2H, J=8.8, 4.8 Hz). Anal. (C$_{15}$H$_{14}$NO$_5$SF.0.2H$_2$O) C, H, N, S.

(b) N-[4-(Hydroxymethyl)-3-methoxyphenyl] 4-fluorobenzenesulfonamide. The title compound was prepared by the reduction of N-[4-(carbomethoxy)-3-methoxyphenyl] 4-fluorobenzenesulfonamide as previously described in Example 17(d). $^1$H NMR (CDCl$_3$) δ: 3.82 (s, 3H), 4.60 (s, 2H), 6.48 (d, 1H, J=8.1 Hz with fine splitting), 6.59 (s, 1H), 6.77 (s, 1H with fine splitting), 7.09–7.28 (m, 3H), 7.77 (m, 2H). Anal. (C$_{14}$H$_{14}$NO$_4$SF.0.15PhCH$_3$) C, H, N, S.

(c) N-(4-[([5-Cyano-6-(5-[2-thienyl]thien-2-yl)-4(3H)-oxopyrimidin-2-yl]thio)methyl]-3-methoxyphenyl) 4-fluorobenzenesulfonamide (23). The title compound was prepared from 5-cyano-6-[5-(2-thienyl)thien-2-yl]-4(3H)-oxopyrimidine-2-thiol and N-[4-(bromomethyl)-3-methoxyphenyl] 4-fluorobenzenesulfonamide as described in Example 1(d). $^1$H NMR (DMSO-d$_6$) δ: 3.75 (s, 3H), 4.37 (s, 3H), 4.37 (s, 3H), 6.60 (d, 1H, J=8.1 Hz with fine splitting), 6.79 (s, 1H, with fine splitting), 7.15 (dd, 1H, J=4.8, 3.7 Hz), 7.28 (d, 1H, J=8.1 Hz), 7.53 (m, 2H), 7.67 (d, 1H, J=5.2 Hz), 7.82 (dd, 2H, J=8.8, 5.1 Hz), 8.19 (d, 1H, J=4.8 Hz), 10.40 (s, 1H). Anal. (C$_{27}$H$_{19}$N$_4$O$_4$S$_4$F.0.8MeOH) C, H, N, S.

Example 24

24

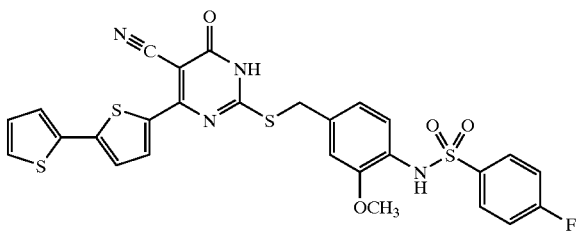

(a) Methyl 4-amino-3-methylbenzoate. A stirred solution of 4-amino-3-methoxybenzoic acid (2.50 g, 14.97 mmol) in MeOH saturated with HCl gas was heated at reflux overnight. The volatiles were removed under reduced pressure and the residue dissolved in EtOAc, washed with saturated NaHCO$_3$ solution, dried over MgSO$_4$ and concentrated under reduced pressure. The title compound was isolated as a tan solid (97%). $^1$H NMR (CDCl$_1$) δ: 3.87 (s, 3H), 3.91 (s, 3H), 4.5 (br s, 2H), 6.73 (d, 1H, J=8.1 Hz), 7.46 (s, 1H, with fine splitting). Anal. (C$_{12}$H$_{11}$NO$_3$) C, H, N.

(b) N-[4-(Carbomethoxy)-2-methoxyphenyl] 4-fluorobenzenesulfonamide. The title compound was prepared from methyl 4-amino-3-methylbenzoate and 4-fluorobenzenesulfonyl chloride as described in Example 15(b). $^1$H NMR (CDCl$_3$) δ: 3.79 (s, 3H), 3.88 (s, 3H), 7.1 (m, 2H), 7.28 (s, 1H), 7.43 (s, 1H with fine splitting), 7.60 (m, 2H), 7.83 (m, 2H). Anal. (C$_{15}$H$_{14}$NO$_5$SF) C, H, N, S.

(c) N-[4-(Hydroxymethyl)-2-methoxyphenyl] 4-fluorobenzenesulfonamide. The title compound was prepared by the reduction of N-[4-(carbomethoxy)-2-methoxyphenyl] 4-fluorobenzenesulfonamide as described in Example 17(d). $^1$H NMR (DMSO-d$_6$) δ: 3.51 (s, 3H), 4.66 (d, 2H, J=5.9 Hz), 5.22 (t, 1H, J=5.9 Hz), 6.87 (d, 1H, J=8.1 Hz), 6.89 (s, 1H), 7.19 (d, 1H, J=8.1 Hz), 7.41 (dd, 2H, J=8.8, 8.8 Hz), 7.78 (dd, 2H, J=8.8, 5.1 Hz), 9.53 (s, 1H). Anal. (C$_{14}$H$_{14}$NO$_4$SF) C, H, N, S.

(d) N4-[([5-Cyano-6-(5-[2-thienyl]thien-2-yl)-4(3H)-oxopyrimidin-2-yl]thio)methyl]-2-methoxyphenyl) 4-fluorobenzenesulfonamide (24). The title compound was prepared from 5-cyano-6-[5-(2-thienyl)thien-2-yl]-4(3H)-oxopyrimidine-2-thiol and N-[4-(bromomethyl)-2-methoxyphenyl] 4-fluorobenzenesulfonamide as described in Example 1(d). $^1$H NMR (DMSO-d$_6$) δ: 3.39 (s, 3H), 4.43 (s, 2H), 6.98 (d, 1H, J=8.1 Hz), 7.07 (s, 1H), 7.14 (d 2H, J=8.7 Hz), 7.31 (dd, 2H, J=8.7, 8.1 Hz), 7.51 (m, 2H), 7.68 (m, 3H), 8.17 (d, 1H, J=3.7 Hz), 9.56 (s, 1H). Anal. (C$_{27}$H$_{19}$N$_4$O$_4$S$_4$F.0.2H$_2$O.0.4EtOAc) C, H, N, S.

Example 25

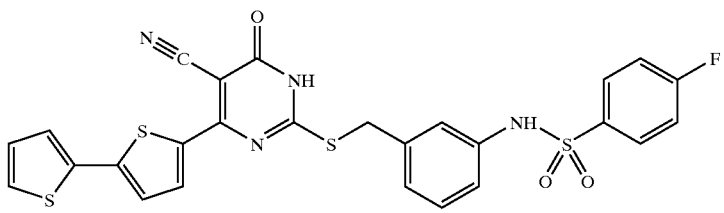

25

(a) N-[3-(Carbomethoxy)phenyl] 4-fluorobenzenesulfonamide. The title compound was prepared from methyl 3-aminobenzoate and 4-fluorobenzenesulfonyl chloride as described in Example 15(b). $^1$H NMR (CDCl$_3$) δ: 1.38 (t, 3H, J=7.0 Hz), 4.37 (q, 2H, J=7.0 Hz), 6.89 (s, 1H), 7.12 (t, 2H, J=8.5 Hz), 7.38 (m, 2H), 7.67 (s, 1H, with fine splitting), 7.80 (m, 3H). Anal. (C$_{14}$H$_{12}$NO$_4$SF) C, H, N, S.

(b) N-[3-(Hydroxymethyl)phenyl] 4-fluorobenzenesulfonamide. The title compound was prepared by the reduction of N-[3-(carbomethoxy)phenyl] (4-fluorophenyl) benzenesulfonamide as described in Example 17(d). $^1$H NMR(CDCl$_3$) δ: 4.39 (s,2H), 6.75 (s, 1H), 6.98 (d, 1H, J=8.1 Hz), 7.09–7.65 (m, 5H), 7.78 (dd, 2H, J=8.8, 4.8 Hz).

(c) N(3-[([5-Cyano-6-(5-[2-thienyl]thien-2-yl)-4(3H)-oxopyrimidin-2-yl]thio)methyl]phenyl) 4-fluorobenzenesulfonamide. The title compound was prepared from 5-cyano-6-[5-(2-thienyl)thien-2-yl]-4(3H)-oxopyrimidine-2-thiol and N-[3-(bromomethyl)phenyl] 4-fluorobenzenesulfonamide as described in Example 1(d). $^1$H NMR (DMSO-d$_6$) δ: 4.51 (s, 2H), 7.01 (d, 1H, J=7.7 Hz), 7.20–7.35 (m, 6H), 7.57 (d, 1H, J=3.7 Hz), 7.59 (s, 1H), 7.72 (d, 1H, J=4.8 Hz), 7.78 (dd, 2H, J=8.8, 5.1 Hz), 8.24 (d, 1H, J=4.4 Hz), 10.42 (s 1H). Anal. (C$_{26}$H$_{17}$N$_4$O$_3$S$_4$F0.5 CH$_2$Cl$_2$) C, H, N, S.

Example 26

(a) Methyl 3-(iodopbenyl)-3-oxopropionate. The title compound was prepared from 3'-iodoacetophenone in a manner described in Example 4(c). $^1$H NMR (CDCl$_3$) δ: 8.27 (1H, dd, J=1.5, 1.8 Hz), 7.95–7.87 (2H, m), 7.22 (1H, dd, J=1.5, 7.7 Hz), 3.97 (2H, s), 3.76 (3H, s). Anal. (C$_{10}$H$_9$O$_3$I) C, H, I.

(b) 6(3-Iodophenyl)-4(3H)-oxopyrimidine-2-thiol. The title compound was prepared from methyl 3-(iodophenyl)-3-oxopropionate and thiourea as previously described in Example 4(d). $^1$H NMR (DMSO-d$_6$) δ: 12.60 (1H, br s), 12.57 (1H, br s), 8.11 (1H, s), 7.96 (1H, d, J=8.1 Hz), 7.75 (1H, d, J=8.1 Hz),7.33 (1H, t, J=8.1 Hz), 6.17 (1H, s). Anal. (C$_{10}$H$_7$N$_2$OSI) C, H, N, S, I.

(c) Methyl 5-[5-([6-(3-iodophenyl)-4(3H)-oxopyrimidin-2-yl]thio)pentyl]thiophene-2-carboxylate. The title compound was prepared from 6-(3-iodophenyl)-4(3H)-oxopyrimidine-2-thiol and methyl 5-(5-bromopentyl) thiophene-2-carboxylate as previously described in Example 1(d). $^1$H NMR (DMSO-d$_6$) δ: 12.75 (1H, br), 8.40 (1H, s), 8.04 (1H, d, J=8.1 Hz), 7.83 (1H, d, J=8.1 Hz), 7.59 (1H, d, J=3.7 Hz), 7.25 (1H, t, J=8.1 Hz), 6.92 (1H, d, J=3.7 Hz), 6.70 (1H, s), 3.77 H, s), 3.19 (2H, t, J=7.3 Hz), 2.85 (2H, t, J=7.4 Hz), 1.79–1.64 (4H, m), 1.52–1.42 (2H, m). Anal. (C$_{21}$H$_{21}$N$_2$O$_3$S$_2$I) C, H, N, S, I.

(d) Methyl 5-[5-([6-(3-cyanophenyl)-4(3H)-oxopyrimidin-2-yl]thio)pentyl]thiophene-2-carboxylate. To a solution of methyl 5-[5-([6-(3-iodophenyl)-4(3H)-oxopyrimidin-2-yl]thio)pentyl]thiophene-2-carboxylate (505 mg, 1 mmol) in THF (25 mL) were added tetrakis (triphenylphosphine)palladium (188 mg, 0.2 mmol) and KCN (195 mg, 3 mmol). The resulting mixture was heated overnight at reflux under an argon atmosphere. After cooling to room temperature, the precipitate was removed by filtration and washed with THF (3×10 mL). The combined filtrates were subsequently concentrated in vacuo to give a yellow gum, which was purified by flash chromatography. Elution with CH$_2$Cl$_2$:CH$_3$OH (97:3) provided the product as a white solid (378 mg, 92% yield). $^1$H NMR (DMSO-d$_6$) δ: 12.87 (1H, br s), 8.46 (1H, s), 8.35 (1H, d, J=8.1 Hz), 7.94 (1H, d, J=7.7 Hz), 7.66 (1H, dd, J=7.7, 8.1 Hz), 7.59 (1H, d, J=3.7 Hz), 6.91 (1H, d, J=3.7 Hz), 6.82 (1H, s), 3.77 (3H, s), 3.24 (2H, t, J=7.2 Hz), 2.83 (2H, t, J=7.3 Hz), 1.80–1.63 (4H, m), 1.51–1.41 (2H, m). Anal. (C$_{22}$H$_{21}$N$_3$O$_3$S$_2$) C, H, N, S.

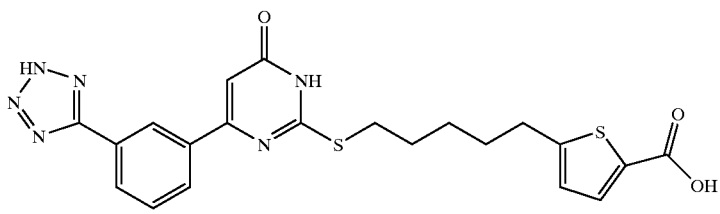

26

(e) Methyl 5-[5-([6-(3-[1(H)-tetrazol-5-yl]phenyl)-4(3H)-oxopyrimidin-2-yl]thio) pentyl]thiophene-2-carboxylate. To a solution of methyl 5-[5-([6-(3-cyanophenyl)-4(3H)-oxopyrimidin-2-yl]thio)pentyl]thiophene-2-carboxylate (303 mg, 0.7 mmol) in DMF (15 ml) were added sodium azide (672 mg, 10 mmol) and ammonium chloride (553 mg, 10 mmol). The reaction mixture was heated at 85° C. for about 16 hours, then poured into water (100 mL). The precipitate that formed was collected by filtration and washed with water (3×15 mL) to provide the product as an orange solid (252 mg, 76% yield). $^1$H NMR (DMSO-d$_6$) δ: 12.84 (1H, br), 8.73 (1H, s), 8.21 (1H, d, J=8.1 Hz), 8.12 (1H, d, J=7.7 Hz), 7.68 (1H, dd, J=7.7, 8.1 Hz), 7.56 (1H, d, J=3.7 Hz), 6.87 (1H, d, J=3.7 Hz), 6.77 (1H, s), 3.76 (3H, s), 3.27 (2H, t, J=7.4 Hz), 2.81 (2H, t, J=7.3 Hz), 1.79–1.61 (4H, m), 1.53–1.46 (2H, m). Anal. ($C_{22}H_{22}N_6O_3S_2 \cdot 0.3H_2O$) C, H, N, S.

(f) 5-[5-([6-(3-[1(H)-Tetrazol-5-yl]phenyl)-4(3H)-oxopyrimidin-2-yl]thio)pentyl]thiophene-2-carboxylic acid (26). Compound 26 was prepared by hydrolysis of methyl 5-[5-([6-(3-[1(H)-tetrazol-5-yl]phenyl)-4(3H)-oxopyrimidin-2-yl]thio)pentyl]thiophene-2-carboxylate in analogy to Example 1(e). $^1$H NMR (DMSO-$d_6$) δ: 12.81 (2H, br), 8.74 (1H, s), 8.23 (1H, d, J=8.1 Hz), 8.13 (1H, d, J=7.7 Hz), 7.69 (1H, dd J=7.7, 8.1 Hz), 7.50 (1H, d, J=3.7 Hz), 6.84 (1H, d, J=3.7 Hz), 6.77 (1H, s), 3.27 (2H, t, J=7.3 Hz), 2.79 (2H, t, J=7.4 Hz), 1.80–1.61 (4H, m), 1.54–1.46 (2H, m). Anal. ($C_{21}H_{20}N_6O_3S_2 \cdot 1.1H_2O$) C, H, N, S.

Example 27

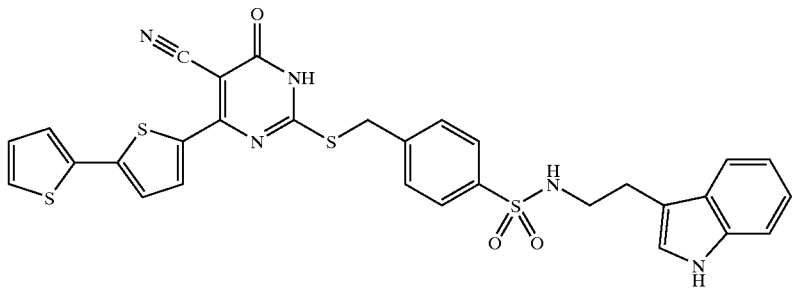

27

N-(2-[1(H)-indol-3-yl]-ethyl) 4-[([5-cyano-6-(5-[2-thienyl]thien-2-yl)-4(3H)-oxopyrimidin-2-yl]thio) methyl] benzenesulfonamide (14). The title compound was prepared from 5-cyano-6-[5-(2-thienyl)thien-2-yl]-4(3H)-oxopyrimidine-2-thiol and N-(2-[1(H)-indol-3-yl]-ethyl) 4-(bromomethyl) benzenesulfonamide generally as described in Example 1(d). N-(2-[1(H)-indol-3-yl]-ethyl) 4-(bromomethyl) benzenesulfonamide was prepared from tryptamine and 4-(bromomethyl)benzenesulfonyl chloride as described in Example 15(b).

BIOCHEMICAL ASSAYS

AICARFT Activity

Enzymatic activity was measured spectrophotometrically using a modified assay developed by Black et al. ("A Rapid Assay for 5-Amino-4-imidazolecarboxamide Ribotide Transformylase," *Anal. Biochiem.* 90 (1978), 397–401). The reaction volume was 1 mL and contained 50 mM Tris-HCl pH 7.5, 25 mM KCl, 20 mM 2-mercaptoethanol, variable concentrations of test compound in 1% DMSO, 50 mM AICAR (5-aminoimidazole-4-carboxamideribonucleotide), 50 mM $N^{10}$-formyl tetrahydrofolate (FTHF), and 0.015 mM enzyme. The reaction was enzyme-initiated and followed by monitoring the increase in absorbance at 298 nm at 25° C. ($\xi_{298}=19.7 \times 10^3$ cm$^{-1}$M$^{-1}$). AICARFT inhibition constants ($K_i$) were determined from the dependence of the steady-state catalytic rate upon compound and substrate concentration. The error associated with this assay is less than 10% of a given $K_i$ value and is often less than 5%. values for compounds of the invention prepared as described above are tabulated below.

| COMPOUND | AICARFT $K_i$ ($\mu$M) |
|---|---|
| 1 | 3.5 |
| 2 | 7.2 |
| 3 | 0.28 |
| 4 | 54.7 |
| 5 | 0.27 |
| 6 | 0.43 |
| 7 | 0.22 |
| 8 | 0.04 |
| 9 | 0.46 |
| 10 | 0.004 |
| 11 | 6.8 |
| 12 | 8.9 |
| 13 | 5.3 |

-continued

| COMPOUND | AICARFT $K_i$ ($\mu$M) |
|---|---|
| 14 | 0.59 |
| 15 | 2.1 |
| 16 | 0.43 |
| 17 | 1 |
| 18 | 0.38 |
| 19 | 0.4 |
| 20 | 1.8 |
| 21 | 0.029 |
| 22 | 1 |
| 23 | 0.77 |
| 24 | 1.3 |
| 25 | 1.4 |
| 26 | 0.37 |
| 27 | 0.083 |

While the invention has been illustrated above in terms of preferred embodiments and specific examples, those skilled in the art will recognize that various changes and modifications can be made without departing from the spirit and scope of the invention. Thus, the invention should be understood as not being limited by the foregoing description, but as being defined by the appended claims and their equivalents.

What is claimed is:

1. A compound having the structure:

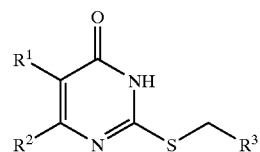
(I)

wherein:

$R^1$ is H or CN;

$R^2$ is phenyl or thienyl, each of which may be optionally substituted with phenyl, phenoxy, thienyl, tetrazolyl, or 4-morpholinyl; and $R^3$ is phenyl substituted by —$SO_2NR^5R^6$ or —$NR^5SO_2R^6$ and optionally further substituted with lower alkyl, lower alkoxy, or halogen, wherein $R^5$ is H or lower alkyl, $R^6$ is lower alkyl, heteroarylalkyl, substituted or unsubstituted with one or more substituents chosen from the group consisting of hydroxy, halogens, oxo, alkyl, acyl, sulfonyl, mercapto, alkylthio, alkoxy, cycloalkyl, heterocycloalkyl, aryl, heteroaryl, carboxy, amino, alkylamino, dialkylamino, carbamoyl, aryloxy, heteroaryloxy, arylthio, and heteroarylthio, substituted or unsubstituted aryl, substituted or unsubstituted heteroaryl, or $R^3$ is

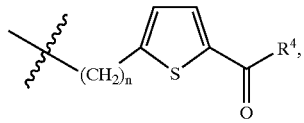

wherein n is an integer of from 1 to 4, R4 is OH, lower alkoxy, or glutamic-acid or glutamate-alkylester linked through the amine functional group, or a pharmaceutically acceptable salt thereof.

2. A compound according to claim 1, wherein aryl and heteroaryl are substituted with lower alkyl, alkoxy or halogen.

3. A compound according to claim 1, wherein aryl is phenyl and heteroaryl is isoquinolyl or indolyl.

4. A compound selected from the group consisting of:

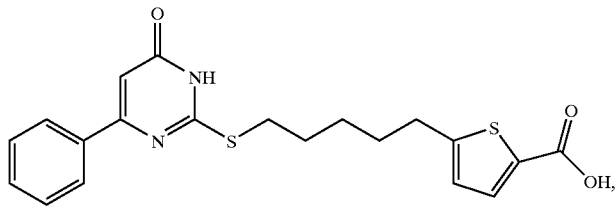

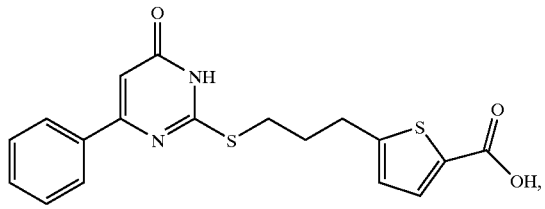

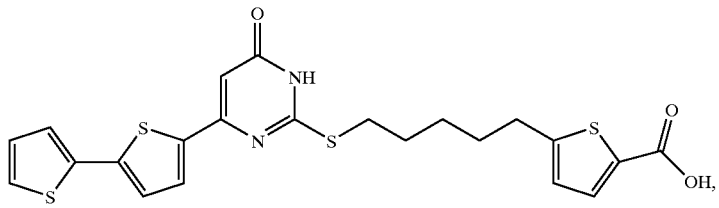

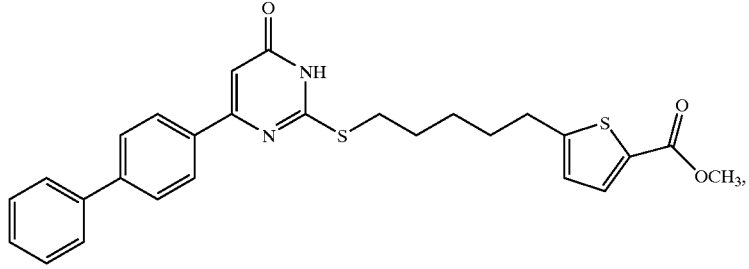

-continued
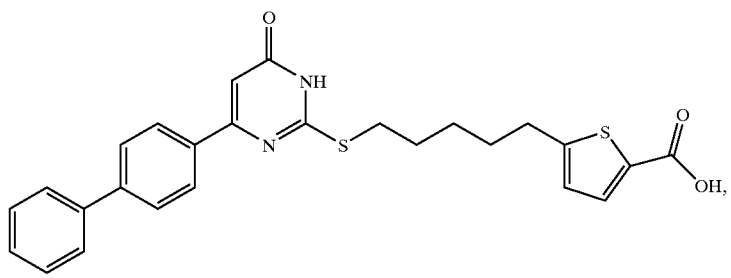
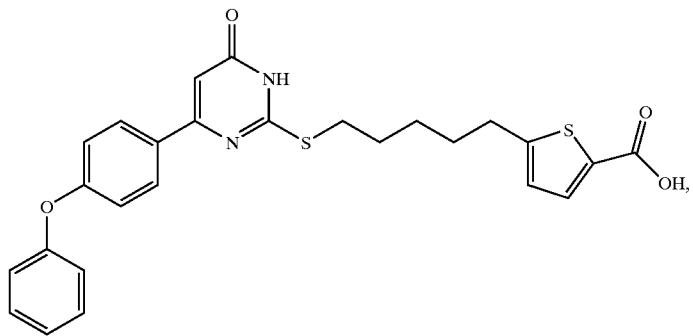
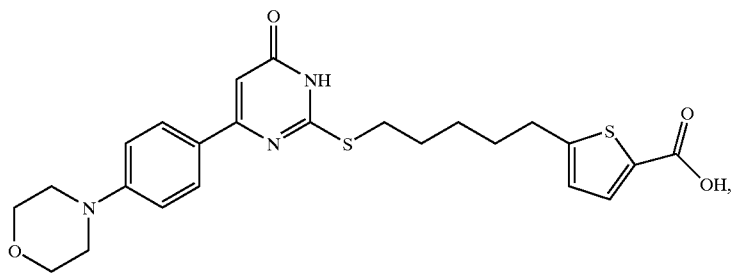
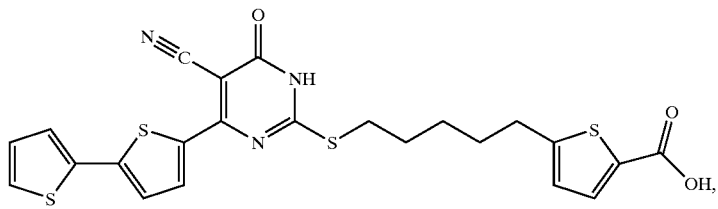
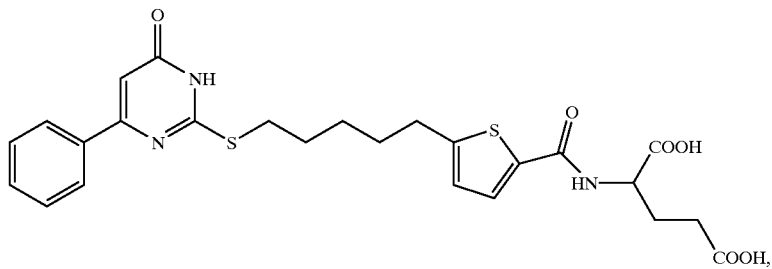
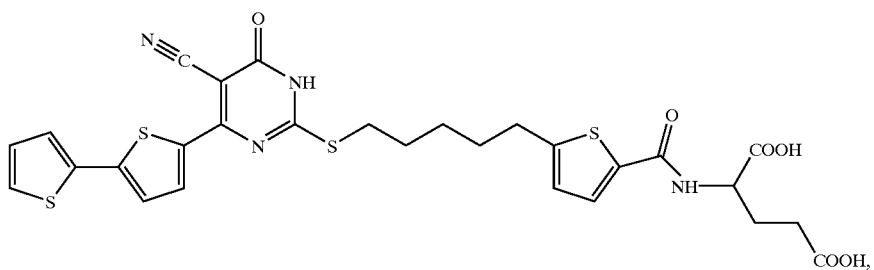

-continued
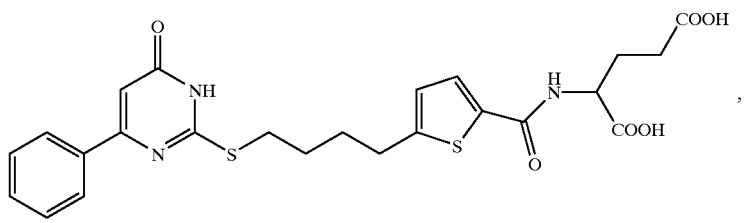
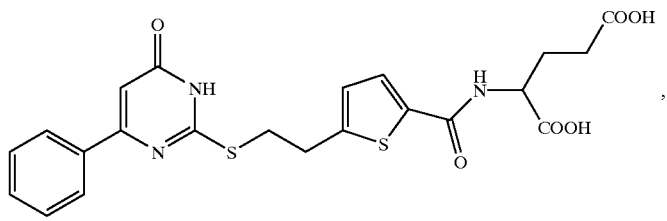
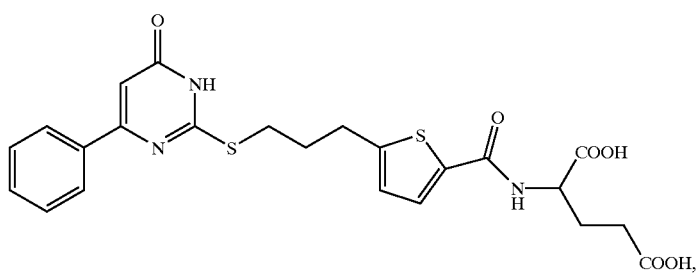
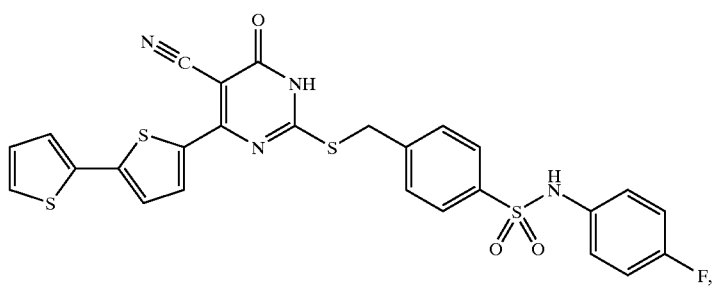
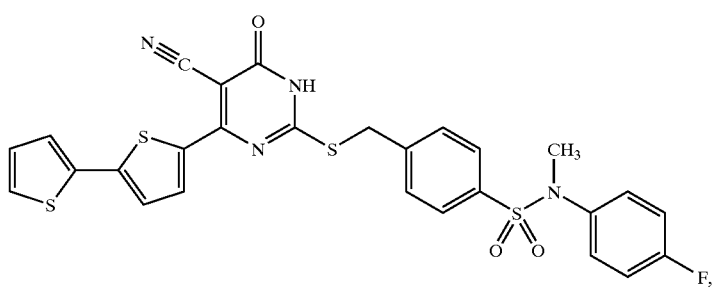
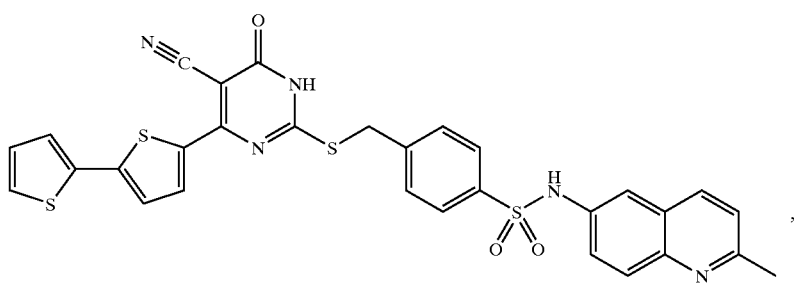

-continued
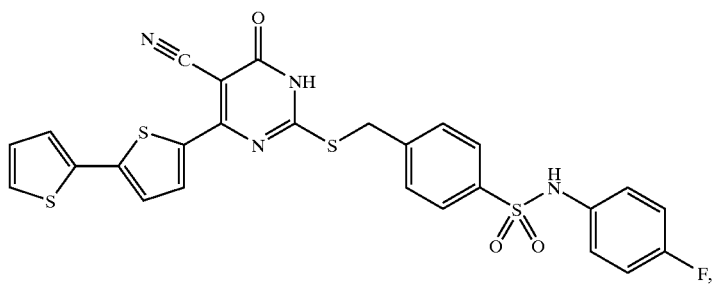
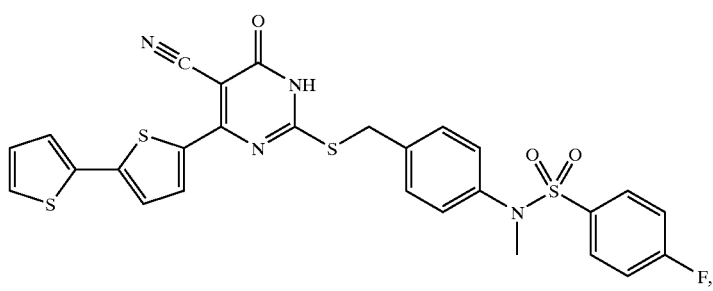
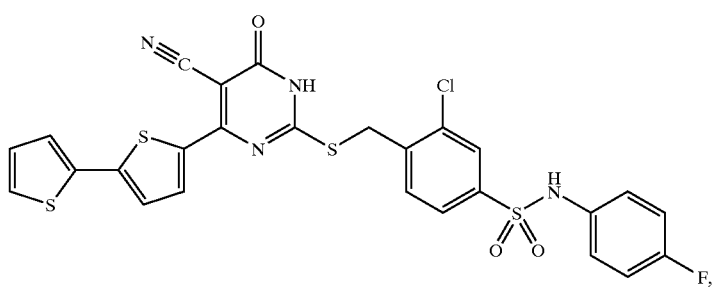
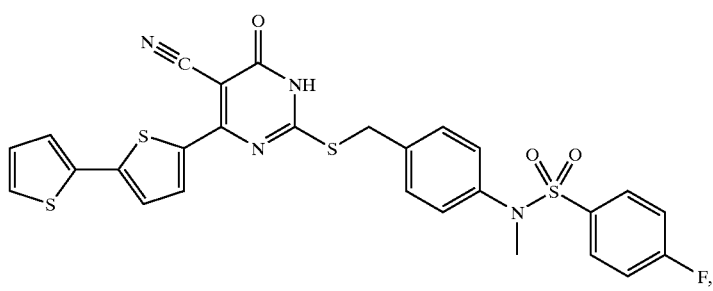
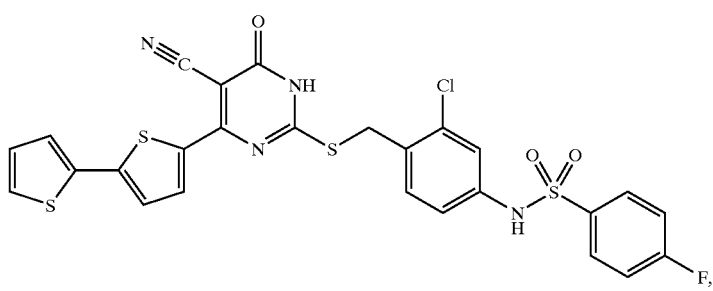
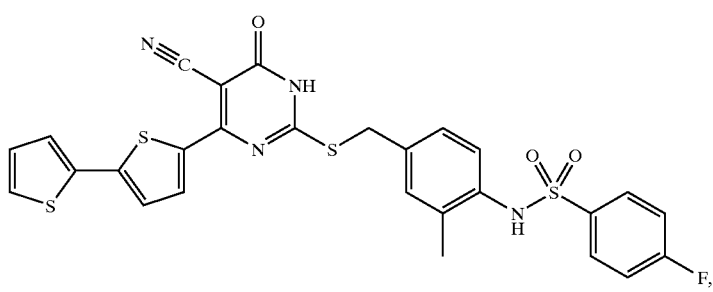

-continued
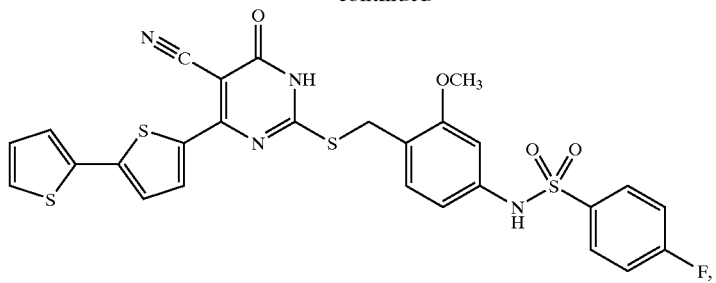
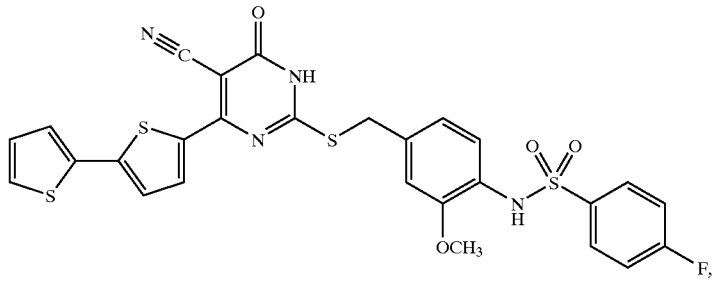
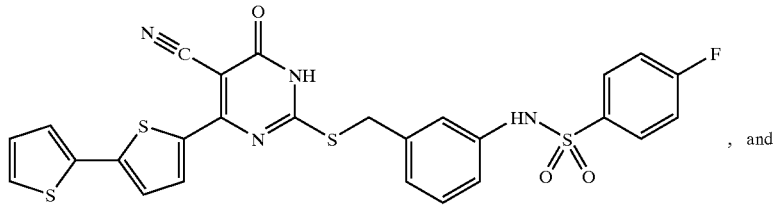
, and
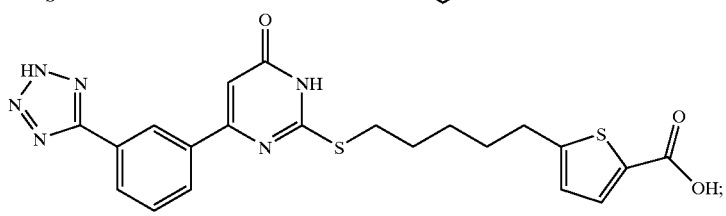
or a pharmaceutically acceptable salt thereof.
* * * * *